United States Patent
Diamond

(10) Patent No.: US 6,727,093 B2
(45) Date of Patent: Apr. 27, 2004

(54) HCMV-REACTIVE T CELLS AND USES THEREFOR

(75) Inventor: Don J. Diamond, Glendora, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 10/238,607

(22) Filed: Sep. 11, 2002

(65) Prior Publication Data

US 2003/0118602 A1 Jun. 26, 2003

Related U.S. Application Data

(63) Continuation of application No. 09/692,170, filed on Oct. 20, 2000, now Pat. No. 6,562,345, which is a continuation-in-part of application No. 09/534,639, filed on Mar. 27, 2000, now Pat. No. 6,251,399, which is a division of application No. 09/075,257, filed on May 11, 1998, now Pat. No. 6,074,645, which is a continuation-in-part of application No. 09/021,298, filed on Feb. 10, 1998, now Pat. No. 6,156,317, which is a continuation-in-part of application No. 08/950,064, filed on Oct. 14, 1997, now abandoned, which is a continuation-in-part of application No. 08/747,488, filed on Nov. 12, 1996, now abandoned.

(51) Int. Cl.[7] ............................... C12N 5/00; C12N 1/12

(52) U.S. Cl. .................... 435/325; 435/69.1; 435/253.1; 424/186.1; 424/204.1; 530/328

(58) Field of Search ........................... 424/186.1, 204.1; 435/325, 64.1, 253.1, 6, 5, 7.1; 530/328

(56) References Cited

U.S. PATENT DOCUMENTS

| 5,075,213 | A | 12/1991 | Pande et al. |
| 5,405,940 | A | 4/1995 | Boon et al. |
| 5,470,730 | A | 11/1995 | Greenberg et al. |
| 5,736,142 | A | 4/1998 | Sette et al. |
| 6,074,645 | A | 6/2000 | Diamond et al. |
| 6,207,161 | B1 * | 3/2001 | Pande et al. ............. 424/186.1 |

FOREIGN PATENT DOCUMENTS

| WO | 92/05794 | | 4/1992 |
| WO | WO 94/00150 | * | 1/1994 |
| WO | 96/06929 | | 3/1996 |
| WO | WO 97/40165 | | 10/1997 |
| WO | WO 98/26074 | | 6/1998 |
| WO | WO 99/19349 | | 4/1999 |
| WO | WO 00/75180 | | 12/2000 |

OTHER PUBLICATIONS

Moldoveanu et al., "CpG DNA, a Novel Immune Enhancer for Systemic and Mucosal Immunization with Influenza Virus," *Vaccine*, 16:11/12:1216–1224, 1998.
Alexander et al., "Development of High Potency Universal DR–Restricted Helper Epitopes by Modification of High Affinity DR–Blocking Peptides," Immunity 1:751–761, Dec. 1994.

Bernhard et al., "Cytotoxic T Lymphocytes from HLA–A2 Transgenic Mice Specific for HLA–A2 Expressed on Human Cells," J. Exp. Med. 168:1157–1162, Sep. 1988.
Berzofsky et al., "Construction of peptides Encompassing Multideterminant Clusters of Human Immunodeficiency Virus Envelope to Induce in Vitro T Cell Responses in Mice and Humans of Multiple MHC Types," The J. of Clinical Investigation, 88:876–884, Sep. 1991.
Boppana et al., "Recognition of Human Cytomegalovirus Gene Products by HCMV–specific Cytotoxic T Cells," Virology 222:293–296, 1996.
Borysiewicz et al., "Relative Frequency of Stage–specific CTL Recognizing the 72–kD Immediate Early Protein and Glycoprotein B Expressed by Recombinant Vaccinia Viruses," J. Exp. Med. 168:919–931, Sep. 1988.
Brouwenstijn et al., "Definition of Unique and Shared T–Cell Defined Tumor Antigens in Human Renal Cell Carcinoma," J. of Immunotherapy 21(6):427–434, 1998.
Chujoh et al., "The role of anchor residues in the binding of peptides to HLA–A*1101 molecules," Tissue Antigens 52:501–509, 1998.
Clay et al., "Changes in the Fine Specificity of $gp100_{(209-217)}$–Reactive T Cells in Patients Following Vaccination with a Peptide Modified at an HLA–A2.1 Anchor Residue," J. of Immunology, pp. 1749–1755, 1999.
Greenberg et al. "Development of a treatment regimen for human cytomegalovirus (CMV) infection in bone marrow transplantatoin recipients by adoptive transfer of donor–derived CMV–specific T cell clones expanded in vitro" in: *Annals of the New York Academy of Sciences* (Antigen and Clone–Specific Immunoregulation) vol. 636:184–195, 1991.
Gyulai et al., "Cytotoxic T Lymphocyte (CTL) Responses to Human Cytomegalovirus pp65, IE1–Exon4, gB, pp150, and pp28 in Healthy Individuals: Reevaluation of Prevalence of IE1–Specific CTLs," The J. of Infectious Diseases 181:1537–46, 2000.
Ishioka et al. "Utilization of MHC Class I transgenic mice for development of minigen DNA vaccines encoding multiple HLA–restricted CTL epitopes" J. Immunology 162:3915–3925, 1999.

(List continued on next page.)

Primary Examiner—Ali R. Salimi
(74) Attorney, Agent, or Firm—Rothwell, Figg, Ernst & Manbeck

(57) ABSTRACT

The invention provides a plurality of peptides (and immunologically functional variants thereof) which are immunogenic epitopes recognized by $CD8^+$ class I MHC restricted cytotoxic T-lymphocytes of patients harboring latent human cytomegalovirus (HCMV) infection. The peptides are capable of activating CTLs and CTLps in the absence of active viral replication, and thus are useful for eliciting a cellular immune response against HCMV by normal and immunodeficient subjects. Peptide and lipopeptide vaccines, with and without adjuvants, also are disclosed. Cellular vaccines comprising the peptides form a further embodiment of this invention.

6 Claims, 10 Drawing Sheets-

OTHER PUBLICATIONS

Kern et al., "Analysis of CD8 T cell reactivity to cytomegalovirus using protein–spanning pools of overlapping pentadecapeptides," Eur. J. Immunol. 30:1676–1682, 2000.

Kern et al., "Target Structures of the CD8+–T Cell Response to Human Cytomegalovirus: the 72 Kilodalton Major Immediate–Early Protein Revisited," J. of Virology 73(10):8179–8184, Oct. 1999.

Lipford et al. "Peptide Engineering Allows Cytotoxic T–cell Vaccination Against Human jPapilloma Virus Tumour Antigen, E6" Immunology 84:298–303, 1995.

Livingston et al. "Altered helper T lymphocyte function associated with chronic hepatitis B virus infection and its role in response to therapeutic vaccination in humans" J. Immunology 162:3088–3095, 1999.

Ohlin et al. "Characterization of human monoclonal antibodies directed against the pp65–kD matrix antigen of human cytomegalovirus" Clin. Exp. Immunol. 84:508–514, 1991.

Oseroff et al. "Pools of lipidated HTL–CTL constructs prime for muliple HBV and HCV CTL eiptope responses" Vaccine 16(8):823–833, 1998.

Panina–Bordignon et al., "Universally immunogenic T cell epitopes: promiscuous binding to human MHC class II and promiscuous recognition by T cells," Eur. J. Immunol. 19:2237–2242, 1989.

Retiére et al., "Generation of Cytomegalovirus–Specific Human T–Lymphocyte Clones by Using Autologous B–Lymphoblastoid Cells with Stable Expression of pp65 or IE1 Proteins: a Tool to Study the Fine Specificity of the Antiviral Response," J. of Virology 74(9):3948–3952, May 2000.

Riddell et al. "Class I MHC–restricted cytotoxic T lymphocyte recognition of cells infected with human cytomegalovirus does not require endogenous viral gene expression" J. Immunology 146(8):2795–2804, Apr. 15, 1991.

Rüger et al. "Primary structure and transcription of the genes coding for the two virion phosphoproteins pp65 and pp71 of human cytomegalovirus" J. Virology 61(2):446–453 Feb. 1987.

Schild et al., "Efficiency of peptides and lipopeptides for in vivo priming of virus–specific cytotoxic T cells," Eur. J. Immunol. 21:2649–2654, 1991.

Theobald et al., "Targeting p53 as a general tumor antigen," Proc. Natl. Acad. Sci. USA 92:11993–11997, Dec. 1995.

Tsunoda et al. "Lipopeptide particles as the immunologically active component of CTL inducing vaccines," Vaccine 17:675–685, 1999.

Vierboom et al. "Peptide Vaccination with an Anchor–Replaced CTL Epitope Protects Against Human Papillomavirus Type 16–Induced Tumors Expressing the Wild–Type Epitope," J. Immunotherapy 2196):399–408, 1998.

Wentworth et al., "Differences and similarities in the A2.1–restricted cytotoxic T cell repertoire in humans and human leukocyte antigen–transgenic mice," Eur. J. Immunol. 26:97–101, 1996.

Wentworth et al. "In Vitro induction of Primary, Antigen–Specific CTL from Human Peripheral Blood Mononuclear Cells Stimulated with Synthetic Peptides," Molecular Immunology 32(9):603–612, 1995.

Quinnan et al., "HLA–Restricted T–Lymphocyte and Non–T–Lymphocyte Cytotoxic Responses Correlate with Recovery from Cytomegalovirus Infection in Bone–Marrow–Transplant Recipients", The New England Journal of Medicine, Cytomegalovirus Infection 307(1): 7–13 (1982).

Borysiewicz et al., "Human Cytomegalovirus–Specific Cytotoxic T Lymphocytes: Requirements for in vitro Generation and Specificity", Eur. J. Immunol. 13:804–809 (1983).

Clark et al., "Isolation and Partial Chemical Characterization of a 64,000–Dalton Glycoprotein of Human Cytomegalovirus", Journal of Virology, Notes 49(1):279–282 (1984).

Forman et al., "A 64,000 Dalton Matrix Protein of Human Cytomegalovirus Induces In Vitro Immune Responses Similar to Those of Whole Viral Antigen", The Journal of Immunology, 134(5):3391–3395 (1985).

Meyers et al., "Risk Factors for Cytomegalovirus Infection After Human Marrow Transplantation", The Journal of Infectious Diseases 153(3):478–488 (1986).

Miller et al., "Retrovirus–Mediated Gene Transfer into Human Skin Fibroblasts", Mar. 1988 Meeting at Cold Spring Harbor.

Borysiewicz et al., "Relative Frequency of Stage–Specific CTL Recognizing the 72–kD Immediate Early Protein and Glycoprotein B Expressed by Recombinant Vaccinia Viruses", J. Exp. Med. 168:919–931 (1988).

Miller et al., "Design of Retrovirus Vectors for Transfer and Expression of the Human β–Globin Gene", Journal of Virology 62(11):4337–4345 (1988).

Townsend et al., "Recognition of Influenza Virus Proteins by Cytotoxic T Lymphocytes", Phil. Trans. R. Soc. Lond. B 323:527–533 (1989).

Gelinas et al., "Regulated Expression of the Human β–Globin Gene After Retroviral Transfer into Murine and Human Hematopoietic Cells", Hemoglobin Switching, Part B: Cellular and Molecular Mechanisms, pp. 235–249 (1989).

Pande et al., "Structural Analysis of a 64–kDa Major Structural Protein of Human Cytomegalovirus (Towne): Identification of a Phosphorylation Site and Comparison to pp65 of HCMV (AD169)", Virology 178:6–14 (1990).

Falk et al., "Allele–Specific Motifs Revealed by Sequencing of Self–Peptides Eluted from MHC Molecules", Nature 351:290–296 (1991).

Schmidt et al., "A Randomized, Controlled Trial of Prophylactic Ganciclovir for Cytomegalovirus Pulmonary Infection in Recipients of Allogeneic Bone Marrow Transplants", The New England Journal of Medicine, 324(15):1005–1011 (1991).

Del Val et al., "Efficient Processing of an Antigenic Sequence for Presentation by MHC Class I Molecules Depends on Its Neighboring Residues in the Protein", Cell 68:1145–1153 (1991).

Penna et al., "Cytotoxic T Lymphocytes Recognize and HLA–A2–Restricted Epitope Within the Hepatitis B Virus Nucleocapsid Antigen", J. Exp. Med. 174:1565–1570 (1991).

Goodrich et al., "Early Treatment with Ganciclovir to Prevent Cytomegalovirus Disease After Allogenei Bone Marrow Transplantation", The New England Journal of Medicine 325(23):1601–1607 (1991).

Reusser et al., "Cytotoxic T–Lymphocyte Response to Cytomegalovirus After Human Allogeneic Bone Marrow Transplantation: Pattern of Recovery and Correlation With Cytomegalovirus Infection and Disease", Blood 78(5):1373–1380 (1981).

Riddell et al., "Restoration of Viral Immunity in Immunodeficient Humans by the Adoptive Transfer of T Cell Clones", Science 257:238–241 (1992).

Missale et al., "HLA–A31 and HLA–Aw68–Restricted Cytotoxic T Cell Responses to a Single Hepatitis B Virus Nucleocapsid Epitope During Acute Viral Hepatitis", J. Exp. Med. 177:751–762 (1993).

Gilbert et al., "Selective Interference with Class I Major Histocompatibility Complex Presentation of the Major Immediate–Early Protein Following Infection with Human Cytomegalovirus", Journal of Virology 67(6):3461–3469 (1993).

Bertoletti et al., "Definition of a Minimal Optimal Cytotoxic T–Cell Epitope within the Hepatitis B Virus Nucleocapside Protein", Journal of Virology 67(4):2376–2380 (1993).

Kast et al., "Human Leukocyte Antigen–A2.1 Restricted Candidate Cytotoxic T Lymphocyte Epitopes of Human Papillomavirus Type 16 E6 and E7 Proteins Identified by Using the Processing–Defective Human Cell Line T2", Journal of Immunotherapy 14:115–120 (1993).

Goodrich et al., "Ganciclovir Prophylaxis To Prevent Cytomegalovirus Disease after Allogeneic Marrow Transplant", Annals of Internal Medicine 118:173–178 (1993).

Winston et al., "Ganciclovir Prophylaxis of Cytomegalovirus Infection and Disease in Allogeneic Bone Marrow Transplant Recipients", Annals of Internal Medicine 118:179–184 (1993).

Riddell et al., "Therapeutic Reconstitution of Human Viral Immunity by Adoptive Transfer of Cytotoxic T Lymphocyte Clones", CurrentTopics in Microbiology and Immunology 189:9–34 (1994).

Li et al., "Recovery of HLA–Restricted Cytomegalovirus (CMV)–Specific T–Cell Responses After Allogeneic Bone Marrow Transplant: Correlation with CMV Diseas and Effect of Ganciclovir Proophylaxis", Blood 83(7):1971–1979 (1994).

Johnson et al., "Induction of a Major Histocompatibility Complex Class I–Restricted Cytotoxic T–Lymphocyte Response to a Highly Conserved Region of Human Immunodeficiency Virus Type 1 (HIV–1) gp 120 in Seronegative Humans Immunized with a Candidate HIV–1 Vaccine", Journal of Virology 68(5):3145–3153 (1994).

Speir et al., "Potential Role of Human Cytomegalovirus and p53 Interaction in Coronary Restenosis", Science 265:391–394 (1994).

McLaughlin–Taylor et al., "Identification of the Major Late Human Cytomegalovirus Matrix Protein pp65 as a Target Antigen for CD8+ Virus–Specific Cytotoxic T Lymphocytes", Journal of Medical Virology 43:103–110 (1994).

Vitiello et al., "Development of a Lipopeptide–based Therapeutic Vaccine to Treat Chronic HBV Infection", J. Clin. Invest. 95:341–349 (1995).

Walter et al., "Reconstitution of Cellular Immunity Against Cytomegalovirus in Recipients of Allogeneic Bone Marrow by Transfer of T–Cell Clones from the Donor", The New England Journal of Medicine 333(16):1038–1044 (1995).

Drijfhout et al., "Detailed Motifs for Peptide Binding to HLA–A*0201 Derived from Large Random Sets of Peptides Using a Cellular Binding Assay", Human Immunology 43:1–12 (1995).

D'Amaro et al., "A Computer Program for Predicting Possible Cytotoxic T Lymphocyte Epitopes Based on HLA Class I Peptide–Binding Motifs", Human Immunology 43:13–18 (1995).

Rasmussen, "Immune Response to Human Cytomegalovirus Infection", Current Topics in Microbiology and Immunology 154:222–254 (1990).

Zhou et al., "Association Between Prior Cytomegalovirus Infection and the Risk of Restenosis After Coronary Atherectomy", The New England Journal of Medicine 335(9):624–630 (1996).

Moss, "Vaccinia Virus Vectors", Construction of Recombinant Viruses, Chapter 15, pp. 345–362.

Pande et al., "Direct DNA Immunization of Mice with Plasmid DNA Encoding the Tegument Protein pp65 (ppUL83) of Human Cytomegalovirus Induces High Levels of Circulating Antibody to the Encoded Protein", Scand J Infect Dis Suppl 99, (Sweden) 1995 p 117–120.

Khattab, B.A. et al., "Three T–Cell Epitopes Within the C–Terminal 265 Amino Acids of the Matrix Protein pp65 of Human Cytomegalovirus Recognized by Human Lymphocytes," Journal of Medical Virology, 52:68–76 (1997).

Ogg, G.H. et al., "HLA–peptide tetrameric complexes," Immunology, 10:393–396 (1998).

Pande, H. et al., "Human Cytomegalovirus Strain Towne pp65 Gene: Nucleotide Sequence and Expression in *Escherichia coli*," Virology 182:220–228 (1991).

Parker, K. et al., "Scheme for Ranking Potential HLA–A2 Binding Peptides Based on Independent Binding of Individual Peptide Side–Chains," Journal of Immunology 152:163–175 (1994).

Wills, M.R. et al., "The human CTL response to Cytomegalovirus is dominated by structural protein," J. Virology 70:(11):7569–7579 (1996).

Tsunoda T. et al., "Seriologically identically HLA B35 alleles which do not cross–present minimal cytotoxic epitopes to CD8+CTL," J. Cell. Biochem. vol. Suppl. 0(19A):298, Abstr. No. J2–218 (1995).

Diamond, D.J. et al., "In vivo priming of virus–specific cytotoxic T lymphocytes with synthetic lipopeptide vaccine," Nature 342:561–564 (1989).

Deres, E.A.: "In vivo priming of virus–specific cytotoxic T lymphocytes with synthetic lipopeptide vaccine," Nature, 342:561–564 (1989).

Gonczol E. et al., "Preclinical evaluation of an ALVAC (canarypox)–human cytomegalovirus glycoprotein B vaccine candidate," Vaccine 13(12):1080–1085 (1995).

Rammensee et al., Immunogenetics 41(4):178–228 (1995).

Livingston et al., J. Immunol. 159:1383–1392 (1997).

* cited by examiner

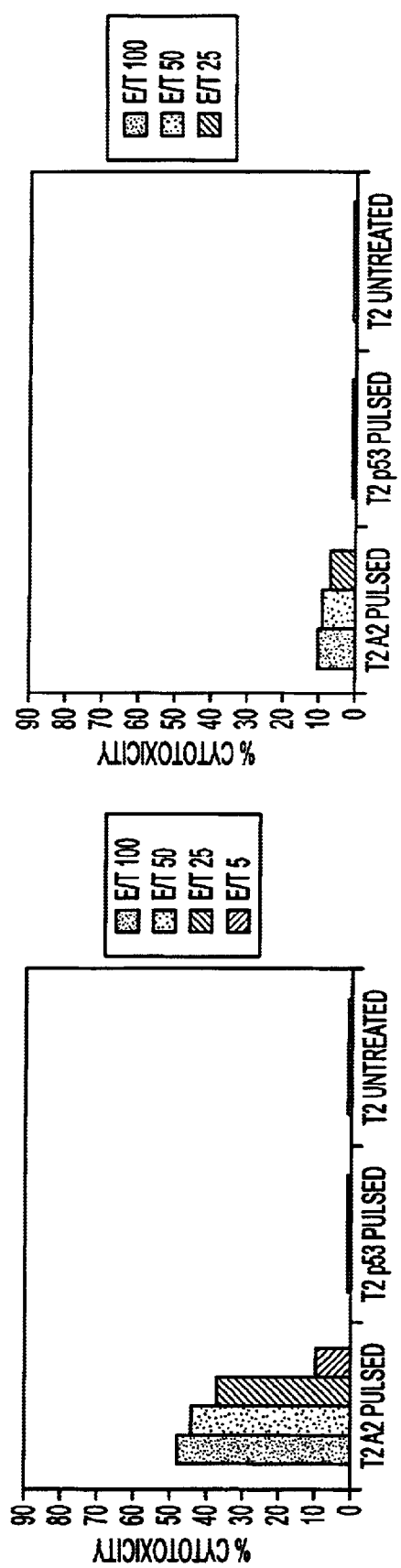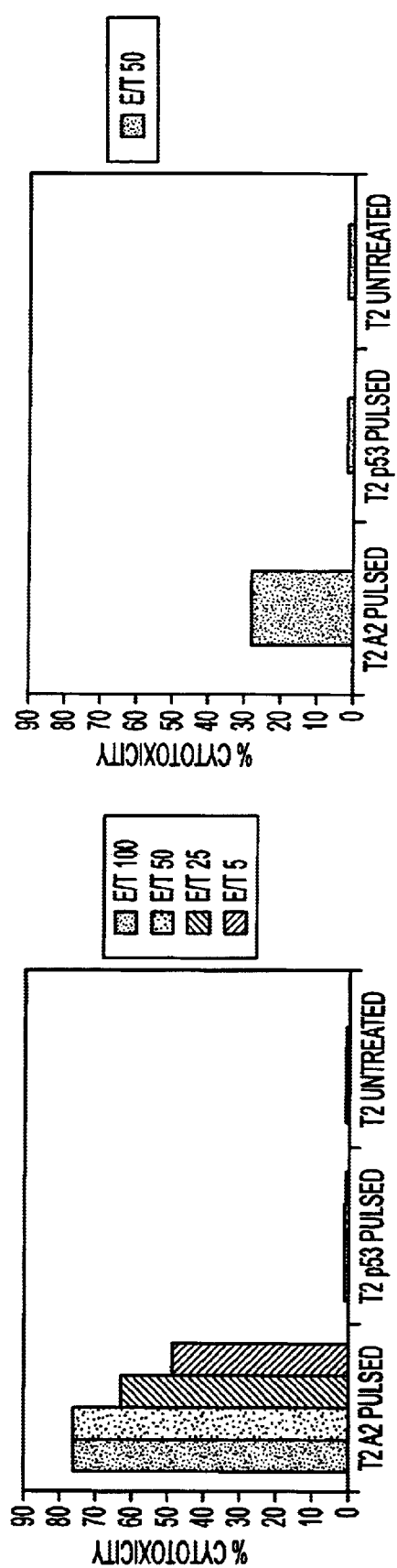

```
                        SEQUENCE LISTING

<160> NUMBER OF SEQ ID NOS: 43

<210> SEQ ID NO 1
<211> LENGTH: 9
<212> TYPE: PRT
<213> ORGANISM: Human cytomegalovirus

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Artificial sequence
<220> FEATURE:
<223> OTHER INFORMATION: Variant human cytomegalovirus peptide epitope
<220> FEATURE:
<221> NAME/KEY: MISC_FEATURE
<222> LOCATION: (2)..(2)
<223> OTHER INFORMATION: Xaa = L, I, M, T or V
<220> FEATURE:
<221> NAME/KEY: MISC_FEATURE
<222> LOCATION: (9)..(9)
<223> OTHER INFORMATION: Xaa = V, A, C, I, L or T

<400> SEQUENCE: 2

Asn Xaa Val Pro Met Val Ala Thr Xaa
1               5

<210> SEQ ID NO 3
<211> LENGTH: 11
<212> TYPE: PRT
<213> ORGANISM: Human cytomegalovirus

<400> SEQUENCE: 3

Tyr Ser Glu His Pro Thr Phe Thr Ser Gln Tyr
```

<210> SEQ ID NO 4
<211> LENGTH: 11
<212> TYPE: PRT
<213> ORGANISM: Artificial sequence
<220> FEATURE:
<223> OTHER INFORMATION: Varian human cytomegalovirus peptide epitope
<220> FEATURE:
<221> NAME/KEY: MISC_FEATURE
<222> LOCATION: (2)..(2)
<223> OTHER INFORMATION: Xaa = S, T or L

<400> SEQUENCE: 4

Tyr Xaa Glu His Pro Thr Phe Thr Ser Gln Tyr
1               5                   10

<210> SEQ ID NO 5
<211> LENGTH: 11
<212> TYPE: PRT
<213> ORGANISM: Human cytomegalovirus

<400> SEQUENCE: 5

Phe Val Phe Pro Thr Lys Asp Val Ala Leu Arg
1               5                   10

<210> SEQ ID NO 6
<211> LENGTH: 11
<212> TYPE: PRT
<213> ORGANISM: Artificial sequence
<220> FEATURE:
<223> OTHER INFORMATION: Variant human cytomegalovirus peptide epitope
<220> FEATURE:
<221> NAME/KEY: MISC_FEATURE
<222> LOCATION: (2)..(2)
<223> OTHER INFORMATION: Xaa = V or T
<220> FEATURE:
<221> NAME/KEY: MISC_FEATURE
<222> LOCATION: (11)..(11)
<223> OTHER INFORMATION: Xaa = L, R or K

<400> SEQUENCE: 6

Phe Xaa Phe Pro Thr Lys Asp Val Ala Leu Xaa
1               5                   10

<210> SEQ ID NO 7
<211> LENGTH: 10
<212> TYPE: PRT
<213> ORGANISM: Human cytomegalovirus

<400> SEQUENCE: 7

Thr Pro Arg Val Thr Gly Gly Gly Ala Met
1               5                   10

<210> SEQ ID NO 8
<211> LENGTH: 10
<212> TYPE: PRT
<213> ORGANISM: Artificial sequence
<220> FEATURE:
<223> OTHER INFORMATION: Variant human cytomegalovirus peptide epitope
<220> FEATURE:
<221> NAME/KEY: MISC_FEATURE
<222> LOCATION: (10)..(10)
<223> OTHER INFORMATION: Xaa = L, F or M

<400> SEQUENCE: 8

Thr Pro Arg Val Thr Gly Gly Gly Ala Xaa
1               5                   10

```
<210> SEQ ID NO 9
<211> LENGTH: 8
<212> TYPE: PRT
<213> ORGANISM: Human cytomegalovirus

<400> SEQUENCE: 9

Phe Pro Thr Lys Asp Val Ala Leu
1               5

<210> SEQ ID NO 10
<211> LENGTH: 11
<212> TYPE: PRT
<213> ORGANISM: Human cytomegalovirus

<400> SEQUENCE: 10

Arg Pro His Glu Arg Asn Gly Phe Thr Val Leu
1               5                   10

<210> SEQ ID NO 11
<211> LENGTH: 12
<212> TYPE: PRT
<213> ORGANISM: Human cytomegalovirus

<400> SEQUENCE: 11

Ser Val Leu Gly Pro Ile Ser Gly His Val Leu Lys
1               5                   10

<210> SEQ ID NO 12
<211> LENGTH: 13
<212> TYPE: PRT
<213> ORGANISM: Human cytomegalovirus

<400> SEQUENCE: 12

Pro Thr Phe Thr Ser Gln Tyr Arg Ile Gln Gly Lys Leu
1               5                   10

<210> SEQ ID NO 13
<211> LENGTH: 10
<212> TYPE: PRT
<213> ORGANISM: Human cytomegalovirus

<400> SEQUENCE: 13

Glu Phe Phe Trp Asp Ala Asn Asp Ile Tyr
1               5                   10

<210> SEQ ID NO 14
<211> LENGTH: 11
<212> TYPE: PRT
<213> ORGANISM: Human cytomegalovirus

<400> SEQUENCE: 14

Phe Thr Ser Gln Tyr Arg Ile Gln Gly Lys Leu
1               5                   10

<210> SEQ ID NO 15
<211> LENGTH: 23
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MISC_FEATURE
<222> LOCATION: (4)..(4)
<223> OTHER INFORMATION: Xaa = cyclohexylalanine
```

-continued

```
<400> SEQUENCE: 15

Ala Ala Lys Xaa Val Ala Ala Trp Thr Leu Lys Ala Ala Ala Asn Leu
1               5                   10                  15

Val Pro Met Val Ala Thr Val
            20

<210> SEQ ID NO 16
<211> LENGTH: 23
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MOD_RES
<222> LOCATION: (1)..(1)
<223> OTHER INFORMATION: dextro
<220> FEATURE:
<221> NAME/KEY: MISC_FEATURE
<222> LOCATION: (4)..(4)
<223> OTHER INFORMATION: Xaa = cyclohexylalanine

<400> SEQUENCE: 16

Ala Ala Lys Xaa Val Ala Ala Trp Thr Leu Lys Ala Ala Ala Asn Leu
1               5                   10                  15

Val Pro Met Val Ala Thr Val
            20

<210> SEQ ID NO 17
<211> LENGTH: 22
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MISC_FEATURE
<222> LOCATION: (3)..(3)
<223> OTHER INFORMATION: Xaa = cyclohexylalanine

<400> SEQUENCE: 17

Ala Lys Xaa Val Ala Ala Trp Thr Leu Lys Ala Ala Ala Asn Leu Val
1               5                   10                  15

Pro Met Val Ala Thr Val
            20

<210> SEQ ID NO 18
<211> LENGTH: 22
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MOD_RES
<222> LOCATION: (1)..(1)
<223> OTHER INFORMATION: dextro
<220> FEATURE:
<221> NAME/KEY: MISC_FEATURE
<222> LOCATION: (3)..(3)
<223> OTHER INFORMATION: Xaa = cyclohexylalanine

<400> SEQUENCE: 18

Ala Lys Xaa Val Ala Ala Trp Thr Leu Lys Ala Ala Ala Asn Leu Val
1               5                   10                  15

Pro Met Val Ala Thr Val
            20
```

```
<210> SEQ ID NO 19
<211> LENGTH: 26
<212> TYPE: PRT
<213> ORGANISM: Artificial sequence
<220> FEATURE:
<223> OTHER INFORMATION: Synthetic construct for human cytomegalovirus
      vaccine

<400> SEQUENCE: 19

Val Ser Thr Ile Val Pro Tyr Ile Gly Pro Ala Leu Asn Ile Ala Ala
1               5                   10                  15

Ala Asn Leu Val Pro Met Val Ala Thr Val
            20                  25

<210> SEQ ID NO 20
<211> LENGTH: 22
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MISC_FEATURE
<222> LOCATION: (3)..(3)
<223> OTHER INFORMATION: Xaa = cyclohexylalanine
<220> FEATURE:
<221> NAME/KEY: MOD_RES
<222> LOCATION: (22)..(22)
<223> OTHER INFORMATION: AMIDATION

<400> SEQUENCE: 20

Ala Lys Xaa Val Ala Ala Trp Thr Leu Lys Ala Ala Ala Tyr Leu Val
1               5                   10                  15

Pro Met Val Ala Thr Val
            20

<210> SEQ ID NO 21
<211> LENGTH: 22
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MOD_RES
<222> LOCATION: (1)..(1)
<223> OTHER INFORMATION: dextro
<220> FEATURE:
<221> NAME/KEY: MISC_FEATURE
<222> LOCATION: (3)..(3)
<223> OTHER INFORMATION: Xaa = cyclohexylalanine
<220> FEATURE:
<221> NAME/KEY: MOD_RES
<222> LOCATION: (22)..(22)
<223> OTHER INFORMATION: AMIDATION

<400> SEQUENCE: 21

Ala Lys Xaa Val Ala Ala Trp Thr Leu Lys Ala Ala Ala Tyr Leu Val
1               5                   10                  15

Pro Met Val Ala Thr Val
            20

<210> SEQ ID NO 22
<211> LENGTH: 22
<212> TYPE: PRT
<213> ORGANISM: Artificial sequence
<220> FEATURE:
<223> OTHER INFORMATION: Synthetic construct for human cytomegalovirus
      vaccine
```

```
<220> FEATURE:
<221> NAME/KEY: MISC_FEATURE
<222> LOCATION: (3)..(3)
<223> OTHER INFORMATION: Xaa = cyclohexylalanine
<220> FEATURE:
<221> NAME/KEY: MOD_RES
<222> LOCATION: (22)..(22)
<223> OTHER INFORMATION: AMIDATION

<400> SEQUENCE: 22

Ala Lys Xaa Val Ala Ala Trp Thr Leu Lys Ala Ala Ala Asn Leu Val
1               5                   10                  15

Pro Met Val Ala Thr Val
            20

<210> SEQ ID NO 23
<211> LENGTH: 22
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MISC_FEATURE
<222> LOCATION: (3)..(3)
<223> OTHER INFORMATION: Xaa = cyclohexylalanine
<220> FEATURE:
<221> NAME/KEY: MOD_RES
<222> LOCATION: (22)..(22)
<223> OTHER INFORMATION: AMIDATION

<400> SEQUENCE: 23

Ala Lys Xaa Val Ala Ala Trp Thr Leu Lys Ala Ala Ala Tyr Leu Val
1               5                   10                  15

Pro Met Val Ala Ser Val
            20

<210> SEQ ID NO 24
<211> LENGTH: 22
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MISC_FEATURE
<222> LOCATION: (3)..(3)
<223> OTHER INFORMATION: Xaa = cyclohexylalanine
<220> FEATURE:
<221> NAME/KEY: MOD_RES
<222> LOCATION: (22)..(22)
<223> OTHER INFORMATION: AMIDATION

<400> SEQUENCE: 24

Ala Lys Xaa Val Ala Ala Trp Thr Leu Lys Ala Ala Ala Asn Leu Leu
1               5                   10                  15

Pro Met Val Ala Ser Val
            20

<210> SEQ ID NO 25
<211> LENGTH: 25
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: MISC_FEATURE
<222> LOCATION: (3)..(3)
<223> OTHER INFORMATION: Xaa = cyclohexylalanine
```

<400> SEQUENCE: 25

Ala Lys Xaa Val Ala Ala Trp Thr Leu Lys Ala Ala Ser Val Leu
1               5                   10                  15

Gly Pro Ile Ser Gly His Val Leu Lys
            20                  25

<210> SEQ ID NO 26
<211> LENGTH: 10
<212> TYPE: PRT
<213> ORGANISM: Human cytomegalovirus

<400> SEQUENCE: 26

Ile Leu Ala Arg Asn Leu Val Pro Met Val
1               5                   10

<210> SEQ ID NO 27
<211> LENGTH: 9
<212> TYPE: PRT
<213> ORGANISM: Human cytomegalovirus

<400> SEQUENCE: 27

Glu Leu Glu Gly Val Trp Gln Pro Ala
1               5

<210> SEQ ID NO 28
<211> LENGTH: 9
<212> TYPE: PRT
<213> ORGANISM: Human cytomegalovirus

<400> SEQUENCE: 28

Arg Ile Phe Ala Glu Leu Glu Gly Val
1               5

<210> SEQ ID NO 29
<211> LENGTH: 13
<212> TYPE: PRT
<213> ORGANISM: Artificial sequence
<220> FEATURE:
<223> OTHER INFORMATION: HTL epitope PADRE
<220> FEATURE:
<221> NAME/KEY: MISC_FEATURE
<222> LOCATION: (3)..(3)
<223> OTHER INFORMATION: Xaa = cyclohexylalanine

<400> SEQUENCE: 29

Ala Lys Xaa Val Ala Ala Trp Thr Leu Lys Ala Ala Ala
1               5                   10

<210> SEQ ID NO 30
<211> LENGTH: 12
<212> TYPE: PRT
<213> ORGANISM: Artificial sequence
<220> FEATURE:
<223> OTHER INFORMATION: Synthetic construct for human cytomegalovirus
      vaccine

<400> SEQUENCE: 30

Lys Ser Ser Asn Leu Val Pro Met Val Ala Thr Val
1               5                   10

<210> SEQ ID NO 31
<211> LENGTH: 12
<212> TYPE: PRT
<213> ORGANISM: Artificial sequence
<220> FEATURE:

```
<223> OTHER INFORMATION: Synthetic construct for human cytomegalovirus
      vaccine
<220> FEATURE:
<221> NAME/KEY: LIPID
<222> LOCATION: (1)..(1)
<223> OTHER INFORMATION: PALMITATE

<400> SEQUENCE: 31

Lys Ser Ser Asn Leu Val Pro Met Val Ala Thr Val
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: LIPID
<222> LOCATION: (1)..(1)
<223> OTHER INFORMATION: DIPALMITATE

<400> SEQUENCE: 32

Lys Ser Ser Asn Leu Val Pro Met Val Ala Thr Val
1               5                   10

<210> SEQ ID NO 33
<211> LENGTH: 29
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: LIPID
<222> LOCATION: (1)..(1)
<223> OTHER INFORMATION: DIPALMITATE

<400> SEQUENCE: 33

Lys Ser Ser Gln Tyr Ile Lys Ala Asn Ser Lys Phe Ile Gly Ile Thr
1               5                   10                  15

Glu Ala Ala Ala Asn Leu Val Pro Met Val Ala Thr Val
            20                  25

<210> SEQ ID NO 34
<211> LENGTH: 29
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: LIPID
<222> LOCATION: (1)..(1)
<223> OTHER INFORMATION: TRIPALMITATE

<400> SEQUENCE: 34

Cys Ser Ser Gln Tyr Ile Lys Ala Asn Ser Lys Phe Ile Gly Ile Thr
1               5                   10                  15

Glu Ala Ala Ala Asn Leu Val Pro Met Val Ala Thr Val
            20                  25

<210> SEQ ID NO 35
<211> LENGTH: 28
<212> TYPE: PRT
<213> ORGANISM: Artificial sequence
<220> FEATURE:
<223> OTHER INFORMATION: Synthetic construct for human cytomegalovirus
```

```
                              vaccine
<220> FEATURE:
<221> NAME/KEY: LIPID
<222> LOCATION: (1)..(1)
<223> OTHER INFORMATION: DIPALMITATE
<220> FEATURE:
<221> NAME/KEY: MISC_FEATURE
<222> LOCATION: (6)..(6)
<223> OTHER INFORMATION: Xaa = F or cyclohexylalanine

<400> SEQUENCE: 35

Lys Ser Ser Ala Lys Xaa Val Ala Ala Trp Thr Leu Lys Ala Ala Ala
 1               5                   10                  15

Gly Gly Gly Asn Leu Val Pro Met Val Ala Thr Val
            20                  25

<210> SEQ ID NO 36
<211> LENGTH: 28
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: LIPID
<222> LOCATION: (1)..(1)
<223> OTHER INFORMATION: TRIPALMITATE
<220> FEATURE:
<221> NAME/KEY: MISC_FEATURE
<222> LOCATION: (6)..(6)
<223> OTHER INFORMATION: Xaa = F or cyclohexylalanine

<400> SEQUENCE: 36

Cys Ser Ser Ala Lys Xaa Val Ala Ala Trp Thr Leu Lys Ala Ala Ala
 1               5                   10                  15

Gly Gly Gly Asn Leu Val Pro Met Val Ala Thr Val
            20                  25

<210> SEQ ID NO 37
<211> LENGTH: 25
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: LIPID
<222> LOCATION: (1)..(1)
<223> OTHER INFORMATION: DIPALMITATE
<220> FEATURE:
<221> NAME/KEY: MISC_FEATURE
<222> LOCATION: (6)..(6)
<223> OTHER INFORMATION: Xaa = F or cyclohexylalanine

<400> SEQUENCE: 37

Lys Ser Ser Ala Lys Xaa Val Ala Ala Trp Thr Leu Lys Ala Ala Ala
 1               5                   10                  15

Asn Leu Val Pro Met Val Ala Thr Val
            20                  25

<210> SEQ ID NO 38
<211> LENGTH: 29
<212> TYPE: PRT
<213> ORGANISM: Artificial sequence
<220> FEATURE:
<223> OTHER INFORMATION: Synthetic construct for human cytomegalovirus
      vaccine
<220> FEATURE:
<221> NAME/KEY: LIPID
<222> LOCATION: (1)..(1)
```

```
<223> OTHER INFORMATION: DIPALMITATE

<400> SEQUENCE: 38

Lys Ser Ser Ile Ser Gln Ala Val His Ala Ala His Ala Glu Ile Asn
1               5                   10                  15

Glu Ala Ala Ala Asn Leu Val Pro Met Val Ala Thr Val
            20                  25

<210> SEQ ID NO 39
<211> LENGTH: 9
<212> TYPE: PRT
<213> ORGANISM: Artificial sequence
<220> FEATURE:
<223> OTHER INFORMATION: Variant human cytomegalovirus peptide epitope
<220> FEATURE:
<221> NAME/KEY: MOD_RES
<222> LOCATION: (9)..(9)
<223> OTHER INFORMATION: AMIDATION

<400> SEQUENCE: 39

Asn Leu Val Pro Met Val Ala Thr Val
1               5

<210> SEQ ID NO 40
<211> LENGTH: 9
<212> TYPE: PRT
<213> ORGANISM: Artificial sequence
<220> FEATURE:
<223> OTHER INFORMATION: Variant human cytomegalovirus peptide epitope
<220> FEATURE:
<221> NAME/KEY: MOD_RES
<222> LOCATION: (9)..(9)
<223> OTHER INFORMATION: AMIDATION

<400> SEQUENCE: 40

Tyr Leu Val Pro Met Val Ala Ser Val
1               5

<210> SEQ ID NO 41
<211> LENGTH: 9
<212> TYPE: PRT
<213> ORGANISM: Artificial sequence
<220> FEATURE:
<223> OTHER INFORMATION: Variant human cytomegalovirus peptide epitope
<220> FEATURE:
<221> NAME/KEY: MOD_RES
<222> LOCATION: (9)..(9)
<223> OTHER INFORMATION: AMIDATION

<400> SEQUENCE: 41

Tyr Leu Val Pro Met Val Ala Thr Val
1               5

<210> SEQ ID NO 42
<211> LENGTH: 20
<212> TYPE: DNA
<213> ORGANISM: Artificial sequence
<220> FEATURE:
<223> OTHER INFORMATION: Synthetic DNA adjuvant

<400> SEQUENCE: 42
tccatgacgt tcctgacgtt                                           20

<210> SEQ ID NO 43
<211> LENGTH: 20
<212> TYPE: DNA
<213> ORGANISM: Artificial sequence
<220> FEATURE:
```

```
<223> OTHER INFORMATION: Synthetic DNA adjuvant

<400> SEQUENCE: 43
tccaggactt ctctcaggtt                                              20
```

HCMV-REACTIVE T CELLS AND USES THEREFOR

This application is a continuation of prior application Ser. No. 09/692,170, filed Oct. 20, 2000, (U.S. Pat. No. 6,562,345), which is a continuation-in-part of prior application Ser. No. 09/534,639, filed Mar. 27, 2000 (U.S. Pat. No. 6,251,399), which is a divisional of Ser. No. 09/075,257, filed May 11, 1998 (U.S. Pat. No. 6,074,645), which is a continuation-in-part of application Ser. No. 09/021,298, filed Feb. 10, 1998, (U.S. Pat. No. 6,156,317), which is a continuation-in-part of application Ser. No. 08/950,064, filed Oct. 14, 1997, now abandoned, which is a continuation-in-part of application Ser. No. 08/747,488, filed Nov. 12, 1996, now abandoned.

STATEMENT REGARDING FEDERALLY SPONSORED RESEARCH

This invention was made with government support in the form of grant nos. CA30206, CA77544 and CA33572 from the United States Department of Health and Human Services, National Cancer Institute. The government may have certain rights in the invention.

BACKGROUND OF THE INVENTION

1. Technical Field

This invention relates to human cytomegalovirus (HCMV), and in particular to peptide fragments from one or more subunit proteins that function as T-cell epitopes of HCMV in human beings. The peptides of this invention are capable of directing human cytotoxic T lymphocytes (CTL) to recognize and lyse human cells equivalently to infection with HCMV. Vaccines formulated using those peptides also are provided by this invention.

2. Description of the Background Art

The HCMV genome is relatively large (about 235 k base pairs) and has the capacity to encode more than two hundred proteins. HCMV is composed of a nuclear complex of double-stranded DNA surrounded by capsid proteins having structural or enzymatic functions, and an external glycopeptide- and glycolipid-containing membrane envelope. HCMV is a member of the herpes virus family and has been associated with a number of clinical syndromes.

HCMV infection is relatively common and is usually self-limiting in the healthy, immunocompetent child or adult (L. Rasmussen, *Curr. Top. Microbiol. Immunol.* 154:221–254, 1990), however, approximately 10% of all newborn infants carry HCMV and the virus can cause severe congenital disease in the fetus or infant. Some of these newborn infants suffer congenital birth defects. Other newborn infants carry cytomegalovirus for some time before they show symptoms of disease. HCMV is a common cause of mental retardation in children who acquire the infection in utero from mothers carrying an active infection.

Several studies have begun to question whether persistent and apparently asymptomatic HCMV infection in an otherwise healthy adult poses health risks in certain individuals. For example, individuals who have undergone coronary angioplasty sometimes subsequently develop restenosis as a result of arterial remodeling. In one study, about one third of such patients with restenosis had detectable HCMV DNA in their arterial lesions (E. Speir et al., *Science* 265:391–394 (1994)). In another study, CMV seropositive patients were five times more likely to develop restenosis than their seronegative counterparts (Y. F. Zhou et al., *New England J. Med.* 335:624–630 (1996)). These studies suggest that decreasing the number of HCMV infected host cells can benefit certain individuals.

HCMV also has been associated with morbidity and mortality in immunocompromised patients. HCMV is an important consideration in the treatment of patients suffering from Acquired Immunodeficiency Syndrome (AIDS). The defining complication is viral retinitis, which, if left untreated, can lead to blindness. Historically, CMV disease has been one of the more devastating of the opportunistic infections that beset HIV-1-infected individuals. Disease manifestations of CMV viremia which appear as the CD4$^+$ T cell counts drops below 100/mm$^3$ include encephalitis, enteritis and pneumonia. At autopsy there is multi-organ involvement of CMV disease in the preponderance of AIDS patients who had severe CMV retinitis. Patients infected with HCMV often suffer impairment of some of their vital organs, including the salivary glands, brain, kidney, liver and lungs. Furthermore, HCMV is associated with a wide spectrum of classical syndromes including mononucleosis and interstitial pneumonia. HCMV also has an oncogenic potential and a possible association with certain types of malignancies including Kaposi's sarcoma.

HCMV can cause opportunistic infections resulting in a variety of complications in, for example, immunosuppressed organ transplant patients. Prior to the use of antiviral chemotherapy, HCMV infection had been responsible for a substantial proportion of post-bone marrow transplantation (BMT) complications (J. Meyers et al., *J. Infect Dis.* 153:478–488 (1986)). The advent of drugs such as ganciclovir with substantial anti-HCMV activity dramatically reduced complications associated with post-BMT CMV infections (G. Schmidt et al. *New England J. Med.* 324:1005–1011 (1991); J. M. Goodrich et al., *New England J. Med.* 325:1601–1607 (1991)).

Ganciclovir is most effective when administered prophylactically before diagnosis of HCMV infection. This approach has several negative consequences, however, including a higher proportion of recipients becoming neutropenic (one third) and increased numbers of concomitant fatal bacterial and fungal diseases (J. M. Goodrich et al., *Ann. Intern. Med.* 118:173–178 (1993)). An alternative approach in which ganciclovir was given when HCMV antigens or DNA are first detected by culture methods provided no survival advantage compared to prophylaxis or treatment post-disease for all patients (D. J. Winston et al., *Ann. Intern. Med.* 118:179–184 (1993)). Finally, because of the acute nature of the side-effects, there is a need for increased hospitalization and growth factor administration to treated patients which, coupled with the cost of ganciclovir prophylaxis, increases the cost of BMT after-care.

Because human cytomegalovirus is relatively common, yet is associated with extremely serious health conditions, a considerable effort has been made to study the biology of the virus with the aims of improving diagnosis of the disease as well as developing preventative and therapeutic strategies. The mounting of a CD8$^+$ CTL response is believed to be an important mammalian host response to certain acute viral infections. The observations that HCMV infection is widespread and persistent, and can become reactivated and clinically evident in the immunosuppressed patient, suggest that virus-specific T-cells, including HCMV-specific CTL, play an important role in the control of persistent infection and in recovery from HCMV disease.

In humans, protection from the development of CMV disease in immunosuppressed BMT recipients correlates with the recovery of measurable CD8+ CMV-specific class I MHC-restricted T cell responses (Quinnan et al., *New Eng. J. Med.* 307:7–13 (1982); Reusser et al., *Blood* 78:1373–1380 (1991)). These observations led investigators to carry out clinical trials in which donor-derived HCMV-specific CD8+ CTL were infused into BMT recipients as an alternative to ganciclovir prophylaxis and therapy (S. R. Riddell et al., *Science* 257:238–241 (1992)). The transfer of CD8+ CTL clones to allogeneic bone marrow transplant recipients resulted in detectable CTL-based HCMV immunity, and statistically significant diminution of HCMV disease after BMT (E. A. Walter et al., *New Eng. J. Med.* 333:1038–1044 (1995)).

Although successful in application, this approach has the disadvantage that it requires a sophisticated laboratory setup (which is also highly labor-intensive and costly) to derive the HCMV-specific CTL in vitro for reinfusion into a patient. A desirable alternative would be to deliver a vaccine derived from HCMV that would impart immunity to a BMT recipient, a solid organ recipient, a heart patient, an AIDS patient or a woman of child-bearing years, without the need for ex vivo expansion of HCMV-specific CTL. No such vaccine presently is available, however. To develop such a vaccine, the viral peptide which cause the host to recognize HCMV in a protective manner must be identified, so that their amino acid sequence information can be determined.

The viral life cycle provides insight as to the most effective time frame for targeting a vaccine to maximally disrupt virus production and spread. Following HCMV entry into the host cell and uncoating, the viral genome is expressed sequentially via immediate early (0–2 hour), early (2–24 hour) and late (>24 hour) viral proteins. However, certain viral structural proteins such as pp65 are chaperoned into the cell because of their existence in large quantity in the viral particle. Much attention has focused upon structural virion proteins as potential immunodominant target antigens for HCMV-specific CTL responses.

One viral structural protein, pp65, has been identified as a target antigen for CMV-specific class I MHC restricted CTL derived from the peripheral blood of most asymptomatic CMV seropositive individuals (E. Mclaughlin-Taylor et al., *J. Med. Virol.* 43:103–110 (1994)). The Immediate Early (IE) protein is processed to form CTL epitopes which cause the stimulation of IE-specific CTL in many normal blood donors (F. Kern et al., *J. Virol.* 73(10):8179–8184 (1999); C. Retiere et al., *J. Virol.* 74(9):3948–3952 (2000); G. Zyulai et al., *J. Infect. Dis.* 181:1537–1546 (2000); F. Kern et al., *Eur. J. Immunol.* 30:1676–1682 (2000). Nevertheless, it has not been shown that IE-specific CTL kill or lyse CMV-infected target cells similarly to CTL specific to structural proteins such as pp65 or pp150. Importantly, CD8+ class I MHC restricted CTL specific for pp65 will recognize autologous HCMV-infected cells without the requirement for viral gene expression, presumably as a result of processing of the internal depot of pp65 that is transferred into the cell during infection (M. J. Gilbert et al., *J. Virology* 67:3461–3469 (1993)). CTL against pp65 or pp150 (another matrix protein that is recognized frequently) are able to recognize and lyse HCMV-infected cells in vitro within an hour of infection in the absence of viral gene expression (S. R. Riddell and P. D. Greenberg, *Curr. Top. Microbiol. Immunol.* 189:9–34 (1994)). Thus, these CTL may represent an important effector cell for limiting HCMV reactivation and progression to CMV disease, and such a cellular immune response in both immunocompromised and normal individuals would be extremely important (C. -R. Li et al., *Blood* 83:1971–1979 (1994)). CTL recognizing envelope proteins are not a substitute for pp65 and pp150 CTL because they are rarely found, arising late in infection and they are poor lytic effectors because of the down-regulation of the required Class I MHC molecules (M. J. Gilbert et al., *J. Virology* 67:3461–3469 (1993)). Therefore, vaccines stimulating immunity against pp65 or pp150 may be the preferred mechanism for eliciting protective immunity against CMV infection.

Individual MHC Class I molecules preferentially bind peptides of a given motif. The amino acid sequence of specific positions of the motif are invariant, allowing a given peptide to bind to MHC Class I molecules with high affinity. These are referred to as "anchor positions" (K. Falk et al., *Nature* 351:290–296 (1991)). Amino acid positions other than the anchor positions also contribute to the specificity of peptide binding to MHC Class I molecules. Additionally, residues at positions within the CTL epitope which do not interact with MHC may nevertheless interact with T cells, presumably by binding the T Cell receptor (TCR). The binding of peptide amino acid residues to MHC or TCR structures is independently governed, so that substitution of TCR binding amino acid residues in many cases will not interfere with binding to the MHC molecule on the surface of an antigen presenting cell.

Edman degradation followed by N-terminal sequence analysis has been used to sequence the peptide mixture which is bound to the MHC class I peptide binding groove. In most cases the length of these peptides is between 9 and 11 amino acids. Mass spectrometry of HPLC separated peptide mixtures can elucidate the primary sequence of individual peptides. Peptide fragments which bind to MHC identified in this manner are referred to as "naturally processed epitopes." Alternatively, one can predict which peptides of a given length, between 9–11 amino acids, will optimally bind to individual HLA Class I alleles based on their conformity to a motif (K. Falk et al., *Nature* 351:290–296 (1991)). One such motif has been established for HLA A*0201. Nonapeptide anchor residues are located at positions 2 and 9 for HLA A*0201, with minor contributions to binding from positions 1, 4, 3, 5, 6, 7, 8 in decreasing order of importance to binding strength (J. W. Drijfhout et al., *Human Immunology* 43:1–12 (1995)). Similar motifs have been established for decamers and undecamers for HLA A*0201. Correspondingly, unique amino acid motifs have been established for a subset of other HLA A and B alleles to predict binding peptides between 8–11 amino acids (H. G. Rammensee et al., *Immunogenetics* 41 (4):178–228 (1995)).

It is recognized that CTL are an important mechanism by which a mammalian organism defends itself against infection by viruses and possibly cancer. A processed form of, e.g., a viral protein minimal cytotoxic epitope (MCE) in combination with MHC Class I molecules is recognized by T cells, such as CD8$^+$ CTL. Functional studies of viral and tumor-specific T cells have confirmed that an MCE of 8–12 amino acids can prime an antigen presenting cell (APC) to be lysed by CD8$^+$ CTL, as long as the APC expresses on the cell surface the correct MHC molecule that will bind the peptide.

It has been shown that the route of entry of a protein into the cell determines whether it will be processed as an antigen bound to either MHC Class I or II molecules. The endogenous or Class I pathway of protein degradation is often used by infectious viruses when they are present within cells. Viral nucleoproteins which may never reach the cell surface as full length molecules are still processed within the cell, and degraded portions are transported to the surface via MHC Class I molecules. Viral envelope glycoproteins, merely because they are cell surface molecules, do not obligatorily induce CTL recognition. Rather, viral nucleoproteins, predominantly in the form of processed epitopes, are the target antigens recognized by $CD8^+$ CTL (A. Townsend et al., *Philos. Trans. R. Soc. Lond.* (*Biol*). 323:527–533 (1989)).

Antigens entering the cell through exogenous pathways (pinocytosis, etc.) are not typically processed and presented by Class I MHC molecules. Therefore, methods to introduce proteins directly into the cytoplasm have become a focus of vaccine developers. An approach that has gained favor is to use recombinant vaccinia viruses to infect cells, delivering a large amount of intracellular antigen. The enthusiasm for using vaccinia viruses as vaccines has diminished, however, because these viruses have the potential to cause disease in immunosuppressed people, such as BMT recipients based on the Western Reserve strain. Another approach to vaccination is to mix an antigenic protein with an adjuvant and introduce the mixture under the skin by subcutaneous injection.

Yet another potential approach to immunization to elicit CTL is to use the MCE defined for a viral antigen in the context of a particular MHC restriction element to boost a CTL memory response to a virus. The ability of an MCE to provide protective immunity to challenge by a lethal dose of an infectious virus has been discussed in the literature. Vaccine developers have developed increasing interest in utilizing the MCE as the vaccine because it is capable of binding to MHC Class I molecules through external binding of the cell surface molecules without internalization or processing.

Historically, the MCE has been most effective as an immunogen when synthesized as a lipidated peptide together with a helper CD4 epitope (A. Vitiello et al., *J. Clin. Invest.* 95:341–349 (1995) and B. Livingston et al., *J. Immunol.* 159:1383–1392, 1997). Other modifications of the bispecific vaccine include inclusion of a signal sequence for endoplasmic reticulum retention and targeting (KDEL) to attain maximum activity. There is also evidence in the literature that an MCE presented by particular types of APC (e.g. dendritic cells) may cause a primary immune response to occur in the absence of viral infection or prior contact with the virus or tumor cell.

Introduction of CMV-specific CTL into a recipient is not a universally applicable and practical strategy to confer immunity to all those at-risk individuals who may need to be immunized against HCMV infection. Accordingly, in spite of significant efforts towards identifying the HCMV proteins that are recognized by CTLs, as well as the specific identification of the HCMV late structural protein pp65, improved methods of preventing and treating HCMV infection are needed.

SUMMARY OF THE INVENTION

Accordingly, one aspect of the present invention relates to immunologically active peptides, and functional variants thereof, capable of eliciting a cellular immune response to HCMV in humans, e.g. SEQ ID NOS: 10–25 and 30–41. The peptides are capable of directing human CTL to recognize and lyse human cells infected with HCMV. Such immunologically active peptides, in association with an MHC Class I molecule, are recognized by CTL of individuals having a latent (inactive) HCMV infection.

Another aspect of the present invention provides a method of augmenting the immune system of a patient in need thereof (i.e., a patient harboring a latent or active CMV infection) by administering at least one immunologically active peptide or peptide derivative according to the present invention that will be recognized by CTL and/or CTLp (CTL precursors) of the patient.

In yet another aspect of the invention, at least one immunologically active peptide is administered to uninfected individuals to provide immunity against future infections by HCMV. Such a peptide may be administered in the form of a peptide or lipopeptide vaccine, optionally with an adjuvant.

Alternatively, the peptide(s) may be administered in the form of a cellular vaccine via the administration of autologous or allogeneic antigen presenting cells or dendritic cells that have been treated in vitro so as to present peptide on their surface.

Yet another aspect of the invention is a method to augment the immune response of an individual who is latently infected with CMV and is at risk for reactivation of CMV infection, wherein T cells are removed from an individual and treated in vitro with a peptide of the present invention. The resulting CMV-reactive CTL are reinfused autologously or allogeneically to the patient, for example, a BMT recipient.

In yet another aspect, a method to confer immunity against an HCMV infection to a previously uninfected individual includes the steps of removing T cells from the individual, exposing the T cells in vitro to a peptide of the present invention and then reinfusing the resulting HCMV-reactive CTL to the individual.

The peptides of the present invention also may be administered to previously infected or uninfected patients, or in vitro to T cells, in the form of a polynucleotide (DNA-based) vaccine, wherein a suitable gene transfer vector, such as a plasmid or an engineered viral vector that contains DNA encoding the peptide fragment under the control of appropriate expression regulatory sequences, is administered to the patient or to T cells in culture.

In yet another of its aspects, the present invention provides a vaccinia, modified Vaccinia Ankara, canarypox or other eukaryotic virus vector containing a DNA sequence encoding the immunologically active peptide fragment, optionally including a helper CD4 epitope in the recombinant virus to stimulate and prolong CTL function. The vector infects an antigen presenting cell which in turn presents antigen that will be recognized by CTLs of patients having a latent (inactive) HCMV infection.

An additional aspect of the invention relates to diagnostic reagents for detection of the presence of active versus quiescent HCMV infections. The peptides according to the present invention can directly stimulate CTLp in vitro and therefore can be used in an assay to determine the degree of immunostimulation being caused by HCMV. The peptides can also be used to distinguish individuals who are seropositive from those who are seronegative. T cells from a patient can be contacted in vitro with antigen presenting cells that have been primed with a peptide according to the present invention.

The invention includes peptides according to SEQ ID NOS: 10–25 and 30–41 and vaccines comprising the peptides of SEQ ID NOS: 1, 10–25 and 30–41. Cellular vaccines also are provided, which comprise antigen presenting cells that have been treated in vitro so as to present a peptide according to any one of SEQ ID NOS: 1, 10–25 and 30–41. Further, the invention comprises a recombinant viral vector vaccine which expresses a gene encoding a peptide according to any one of SEQ ID NOS: 1–14, 19, 26–28 and 30. In addition, a further embodiment comprises a method of modulating the immune response to human cytomegalovirus infection, comprising administering a vaccine as described above.

BRIEF DESCRIPTION OF THE DRAWING

FIG. 8 compares the cytoxicity data for cells immunized with SEQ ID NO:37 in different vaccine formulations.

DETAILED DESCRIPTION OF THE PREFERRED EMBODIMENTS

Figure 1:
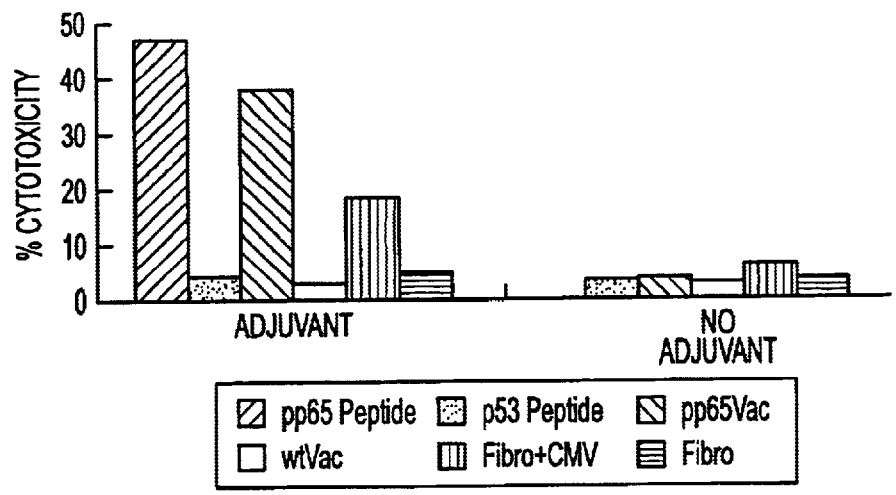
FIG. 1 shows the cytotoxic response elicited by peptides in the absence of lipidation.

A nonapeptide having the sequence NLVPMVATV ($pp65_{495\text{-}503}$) (SEQ ID NO:1) is an immunogenic epitope of pp65 from CMV laboratory strains AD169 and Towne and all wild type isolates examined to date. The epitope is recognized by $CD8^+$ Class I MHC restricted cytotoxic T-lymphocytes of patients harboring latent CMV infection. The peptide is capable of activating CTL in the absence of active viral replication, and thus is useful for augmenting the immune system of both normal and immunodeficient patients, as well as in the study of the Class I antigen processing pathway for HCMV proteins. The amino acid residues in positions 2 and 9 are the preferred residues at those positions for interaction with HLA A*0201 and certain subtypes of HLA A*02XX, where XX=subtypes 02–22 (J. W. Drijfhout et al., *Human Immunology* 43:1–12 (1995)). Nonetheless, other less preferred amino acid residues may replace the preferred anchors, and the peptide can continue to exhibit the capacity to bind HLA A*0201 and certain subtypes of HLA A*02XX and to stimulate HCMV-specific $CD8^+$ CTL.

Thus, in one aspect, the present invention provides an immunologically active peptide, capable of eliciting a cellular immune response to human cytomegalovirus infection, of the preferred sequence:
NLVPMVATV (SEQ ID NO:1).
Sequence variants of the preferred peptide include peptides of the sequence $NX_1VPMVATX_2$ wherein $X_1$ is L,I,M,T or V, and $X_2$ is V,A,C,I,L or T (SEQ ID NO:2). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein, for example AAKXVAAWTLKAAANLVPMVATV wherein X is cyclohexylalanine; SEQ ID NO:15 or (d)AAKXVAAWTLKAAANLVPMVATV where X signifies cylohexylalanine (SEQ ID NO:16).

Other immunologically active peptides according to the present invention include the peptides:
YSEHPTFTSQY (SEQ ID NO:3)
which binds to HLA A*01XX including A*0101 and subtypes thereof. Sequence variants of this peptide include peptides of the sequence YXEHPTFTSQY wherein X is S, T or L (SEQ ID NO:4). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.
FVFPTKDVALR (SEQ ID NO:5)
which binds to HLA A*68XX including A*6801 and subtypes thereof. Sequence variants of this peptide include peptides of the sequence $FX_1FPTKDVALX_2$ wherein $X_1$ is V or T and $X_2$ is L, R or K (SEQ ID NO:6). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.
TPRVTGGGAM (SEQ ID NO:7)
which binds to HLA B*07XX including B*0702 and subtypes thereof. Sequence variants of this peptide include peptides of the sequence TPRVTGGGAX wherein X is L, F, or M (SEQ ID NO:8). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.
FPTKDVAL (SEQ ID NO:9)
which binds to HLA B*35XX including B*3502, B*3504, B*3506 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.
RPHERNGFTVL (SEQ ID NO:10)
which binds to HLA B*07XX including B*0702 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.
SVLGPISGHVLK (SEQ ID NO:11)
which binds to HLA A*11XX including A*1101 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

PTFTSQYRIQGKL (SEQ ID NO:12)

which binds to HLA B*3801/2 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

EFFWDANDIY (SEQ ID NO:13)

which binds to HLA B*44XX including B*4402 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

FTSQYRIQGKL (SEQ ID NO:14)

which binds to HLA A*24XX including A*2402 and other subtypes thereof with compatible binding sites. The invention includes the construction and selection of other functional sequence variants such as TFTSQYRIQGKL (SEQ ID NO:26), which can be carried out by those skilled in the art based upon the present disclosure. The peptide or structural variants disclosed herein also can be a functional part of a longer peptide which produces the immunological effects disclosed herein.

The following constructs exemplify peptide vaccines according to the invention and are not intended to be limiting:

AKXVAAWTLKAAANLVPMVATV (SEQ ID NO:17)
dAKXVAAWTLKAAANLVPMVATV (SEQ ID NO:18)
VSTIVPYIGPALNIAAANLVPMVATV (SEQ ID NO:19)
AKXVAAWTLKAAAYLVPMVATV-NH$_2$ (SEQ ID NO:20)
dAKXVAAWTLKAAAYLVPMVATV-NH$_2$ (SEQ ID NO:21)
AKXVAAWTLKAAANLVPMVATV-NH$_2$ (SEQ ID NO:22)
AKXVAAWTLKAAAYLVPMVASV-NH$_2$ (SEQ ID NO:23)
AKXVAAWTLKAAANLLPMVASV-NH$_2$ (SEQ ID NO:24)
AKXVAAWTLKAAASVLGPISGHVLK (SEQ ID NO:25)

wherein X=cyclohexylalanine and d=dextro.

Truncations of the pp65 (Diamond et al. 1997) protein expressed in vaccinia viruses were screened against pp65-specific T cell (CD8$^+$) clones from HLA typed CMV-seropositive individuals (Walter et al., *New Engl. J. Med.* 333:1038–1044 (1995); McLaughlin-Taylor et al., *J. Med. Virol.* 43:103–110 (1994). To facilitate fine scale mapping of CTL epitopes, recombinant vaccinia viruses have been prepared that express pp65 fragments separated by 100–200 nucleotides throughout the pp65 gene, with both amino and carboxyl terminal deletions. When the region circumscribed by recombinant vaccinia viruses was no greater than 100 amino acids, a series of overlapping peptides were synthesized. A series of 15 mer peptides from pp65, overlapping by three amino acids, were used to identify CTL epitopes. Longmate et al., *Immunogenetics* (2000). Screening a 100 amino acid stretch of pp65 in this way requires a total of 29 different peptides. Autologous and HLA mismatched Epstein-Barr virus transformed lymphocyte cell lines (antigen presenting cells) were sensitized with the screening peptides at a concentration of 50 μM for 1–2 hours, washed and chromated. The relevant CTL clone was incubated with the lymphocyte cell lines sensitized with peptide, and a standard chromium release assay was performed to determine the sensitivity of lysis. Peptide(s) which successfully sensitized lymphocytes to lysis by the pp65-specific T cell clones were then further truncated, both at the amino and carboxyl termini and retested. These steps were repeated until the minimal cytotoxic epitope that corresponds to the HLA allele of the T cell clones used was defined. Exemplary epitopes of pp65 are shown in Table 6.

Using the methods outlined above, peptides suitable for vaccine production can be identified for T cell clones from individuals having a variety of haplotypes. In this way, a cocktail vaccine useful to vaccinate large multi-ethnic human populations may be created. If a vaccine has broad enough reactivity to be usable for at least 90% of most ethnic populations, it is suitable to be used for public health. A multi-epitope peptide vaccine against HCMV would be very beneficial to several different at-risk patient groups including transplant recipients, AIDS patients, and gestational fetuses, not all of whom have been HLA-typed.

Peptides according to the invention may be formulated as vaccines according to any suitable method. Naked peptides or lipidated peptides may be formulated in a suitable adjuvant or any other pharmaceutically acceptable carrier. Cellular vaccines may be prepared by any known method. HCMV peptides according to the invention may be administered alone, or together with a helper peptide such as the polyclonal helper T lymphocyte peptide, PADRE. The CTL epitope and HTL peptide may be administered together or separately, but it is preferable to administer them in close time proximity.

Alternative vaccines include fusions of the helper CD4 peptide epitope with the CTL epitope. The peptides may be fused in either order and may contain a linker sequence between them if desired. Examples of helper CD4 epitopes are the synthetic sequence PADRE (J. Alexander et al., *Immunity* 1:751–761 (1994)) and tetanus-specific peptides, however any helper T lymphocyte peptide may be used. In some cases, these fusion peptides may not require additional covalent lipid modification or adjuvant when administered by the subcutaneous, intranasal, intraperitoneal or intravenous routes. Alternatively, single stranded DNA containing CpG motifs or any other adjuvant may be co-administered to provide increased activity of the fusion peptide when simultaneously provided at limiting concentration.

A preferred alternative is to join the antigenic peptide to PADRE such that the two sequences form a single peptide chain. PADRE may be positioned at the N- or C-terminus of the antigenic HCMV peptide, and a linker sequence may be positioned between the two sequences or in front of the N-terminal sequence, if desired. A preferred structure for this type of vaccine peptide is AAKXVAAWTLKAAAN-LVPMVATV wherein X signifies cyclohexylalanine (SEQ ID NO:15) or (d)AAKXVAAWTLKAAANLVPMVATV wherein X signifies cylohexylalanine (SEQ ID NO:16).

Peptides of the invention may be lipidated or may lack lipids. Unlipidated peptides, whether incorporating a helper peptide sequence or not, are contemplated by the invention, as are monolipidated, dilipidated or trilipidated peptide vaccines. Suitable lipids which may be linked to the peptide sequence include, but are not limited to palmitic acid, stearic acid, myristic acid, lauric acid, capric acid, decanoic acid and the like. Lipids may be attached to the peptides at any location and by any convenient method known in the art.

Adjuvants may form part of the vaccine formulation. Adjuvants such as complete or incomplete Freund's adjuvant, aluminum hydroxide or the like are contemplated, however a preferred adjuvant, particularly for use in humans, is a DNA adjuvant. Single-stranded DNA adjuvants comprising specific sequences including Cytosine-phosphate-Guanosine (CpG) are known in the art and are contemplated for use with this invention. DNA adjuvants lacking these CpG sequences also are useful with the invention. An exemplary DNA adjuvant may comprise a 20 mer of nucleotides with 2 CpG motifs, or any DNA oligomer, generally about 20 to about 25 nucleotides long. Increased stability of the sequence may be obtained by substituting phosphate groups in the nucleotide backbone with two groups to create a phosphoro-thioate backbone rather than a phosphoro-diester backbone.

Evaluation of HCMV peptide-specific human CTL responses may be performed in HLA-A2.1/$k^b$ transgenic mice, a well-accepted animal model, as follows. The mice are injected with the vaccine preparation. A booster may be given 12 days later if desired. About one week after the final immunization, splenocytes are prepared from the spleens of immunized mice and cultured. Lipopolysaccharide (LPS) blasts for in vitro stimulation of the immunized cells may be prepared aseptically from suspensions of unimmunized mouse spleen cells ($1.0-1.5\times10^6$ cells/mL) by addition of 25 µg/mL LPS and 7 µg/mL dextran sulfate. These cells are loaded with the same CTL epitope peptide as was used to immunize the transgenic mice to create antigen-presenting cells. These antigen-presenting cells are used to stimulate the cultured splenocytes from the immunized transgenic mice in vitro approximately 12–14 days after the final immunization. A second in vitro stimulation, or further in vitro stimulations, may be performed if desired. A second stimulation is preferred, and may be performed 5–7 days after the first in vitro stimulation. About a week after the last in vitro stimulation, a chromium release assay may be performed to test the ability of the immunized transgenic splenocytes to specifically recognize and kill either mouse or human target cells loaded with the antigenic peptide of the vaccine.

EXAMPLE 1

Derivation of T-cell Clones

Methods for deriving T-cell clones from CMV seropositive individuals have been described in the literature (see above references). Forty to fifty milliliter samples of whole peripheral blood were obtained from CMV seropositive volunteers (detected by standard antibody methods). The white blood cells (WBCs) were separated using Ficoll-HyPaque (DuPont) density gradient centrifugation. The whole blood was first centrifuged for 10 minutes at 1400 rpm in a tabletop centrifuge to reduce the number of red blood cells. The buffy coat was diluted to 12 ml with phosphate buffered saline (PBS), and 6 ml were layered on top of ½ volume of Ficoll-HyPaque. The top layer was removed after centrifugation at 2000 rpm in a tabletop centrifuge for 15–30 minutes. The interface containing the WBC was removed, diluted in PBS and recentrifuged for 8–12 minutes at 1000 rpm, which caused the WBC to pellet. The cells were again resuspended in PBS and washed as above one additional time. Four to five million WBC/ml were resuspended in T cell medium (TCM) with human serum obtained from pooled AB+ (blood group) CMV seronegative donors (HAB).

EXAMPLE 2

Derivation of LCL Antigen-Presenting Cells

Simultaneously, an autologous antigen presenting cell line was prepared by Epstein Barr virus immortalization of PBL (see Current Protocols in Immunology, Unit 7.22, Wiley-Liss Press (1993)). Deriving the CTLs and antigen presenting cells from the same individual ensured HLA matching between the cell lines.

EXAMPLE 3

In vitro Stimulation by HCMV

To initiate the in vitro stimulation of the WBC, a monolayer of autologous dermal fibroblasts obtained from the same volunteers as the WBC was established by plating the cells in 12-well plates at $10^5$ cells/ml/well in DMEM-10% HAB for 24 hours. After 24 hours in culture the fibroblasts were infected with CMV virions (AD169 or Towne strain) for 2 hours at a multiplicity of infection of between 1 and 5. The medium and virus were aspirated from the monolayer, and 1 ml of fresh DMEM-HAB was added. The monolayer was incubated in the medium for an additional 4 hours, following which time, the medium was aspirated. Two milliliters of medium containing 8–10 million WBC were added per well containing CMV infected fibroblasts. The WBC and fibroblasts were cultured in RPMI-1640 (Irvine Scientific) containing 50 U/ml penicillin, 50 µg/ml streptomycin, 4 mM L-glutamine, 25 µM 2-mercaptoethanol, 10 mM HEPES and 10% HAB (TCM-HAB). This was termed the first stimulation, and the cells were co-incubated for seven days. TCM-HAB was replaced if it became spent, and the culture was expanded if there was vigorous cell growth.

The WBC were re-stimulated on day 7 by plating onto a fresh monolayer of HCMV-infected autologous fibroblasts prepared as described above. In addition, γ-irradiated (2500 rad) autologous PBL (5-fold over WBC) were added as feeder cells, and the medium was supplemented with recombinant IL-2 (10 IU/ml, Chiron-Cetus) on days 2 and 4 of this second stimulation. Wells which exhibit rapid cell growth require new medium containing IL-2 as the medium became spent.

After 12–16 days in culture, the cells were harvested and assayed for recognition of CMV matrix proteins in a chromium release assay (CRA). The CRA was performed using antigen presenting cells as target cells which are autologous or HLA-mismatched to the T-cell clone. The cells were prepared by infection with recombinant vaccinia viruses containing the DNA for HCMV proteins such as pp28 (pp28vac), pp65 (pp65vac) and pp150 (pp150vac) or wild-type virus strain WR.

After overnight infection, the antigen presenting cells were incubated with chromium-51, washed, and the assay was carried out as described in Current Protocols in Immunology, Wiley-Liss Press, Unit 7.17, (1993). In the CRA, the vaccinia-infected target cells were loaded with chromium-51 and then mixed with cells from the T-cell clone (effector cells). The cells were mixed at a series of effector : target cell ratios varying from 20:1 to 1:1. After a 4 hour incubation period, the medium in which the cells were incubated was harvested. The release of radioactivity into the medium (Re) was quantitated with a gamma scintillation counter. The extent to which infected antigen presenting cells exhibit spontaneous lysis and the release of radioactivity ($R_s$) in the absence of CTL was established for each virus vector. The maximum amount of radioactivity incorporated into and releasable by the target cells ($R_{max}$) was established by lysis of target cells in a detergent (1% Triton X100; Sigma) solution. Percentage cytotoxicity was expressed as:

$$100 \times ((R_e)-(R_s))/((R_{max})-(R_s)).$$

Assays were deemed unacceptable and were repeated unless spontaneous release ($R_s$) was less than 30%.

Analysis of the assay was as described, with a positive result indicated by specific recognition of pp65vac infected autologous APC. A positive result for pp65 indicated that, in the tested polyclonal population, there were T cells which recognize the pp65 HCMV protein expressed by the virus.

EXAMPLE 4

Procedure for Identification of the CTL Epitope

WBC stimulated two times by HCMV on dermal fibroblasts were cloned by limiting dilution in 96 well U-bottom plates as follows. After two HCMV stimulations, the WBC were depleted of CD4$^+$ T cells by negative selection using incubation with paramagnetic beads conjugated to anti-CD4 antibodies. The resulting population was generally between 90–95% CD8$^+$, a reliable T cell subset marker, and generally 99% CD3$^+$, a marker for most peripheral blood T cells as assayed by either flow cytometry or fluorescence microscopy. This final population was plated at a concentration between 0.3–3 cells per well in a final volume of 150 $\mu$l. Each well also contained $\gamma$-irradiated $1.0$–$3.0 \times 10^5$ allogeneic peripheral blood mononuclear cells (PBMC) in TCM-HAB supplemented with 50–100 IU/ml recombinant IL-2 (Chiron-Cetus) and 0.5 $\mu$g/ml PHA (Murex).

After 3 days of culture, the PHA was diluted 2-fold by exchanging 75 $\mu$l with fresh culture medium supplemented with rIL-2. The wells were supplemented with fresh rIL-2 every 3–4 days, and medium was replaced as necessary. The cells were restimulated 12–14 days later with fresh allogeneic PBMC as described above, and the plates were carefully observed for growth in individual wells. Visible cell growth indicated the need to transfer the expanding T cells to larger wells. T cells were restimulated every two weeks, and were transferred to progressively larger wells. At the stage of accumulation of several million cells, some were cryopreserved, and others were subjected to a further CRA. In this CRA, the targets were HCMV infected fibroblasts, uninfected fibroblasts, or autologous LCL infected with wild type vaccinia or vaccinia virus expressing either pp28, pp65 or pp150. HLA mismatched fibroblasts and LCL were used as controls. One T cell clone among several tested, which was designated 3-3F4, had the characteristics of being both CMV and pp65-specific, and was reactive only to autologous targets in a specific manner. Other T cell clones with different HLA phenotypes were initially isolated in the same way, except that the initial peripheral blood sample came from different volunteers.

The HLA element which restricted the recognition of the T cell clone 3-3F4 to pp65 was identified. A series of LCL were used as targets that were singly autologous with each HLA allele of the 3-3F4 cell line. Each target was separately infected with pp65vac, wild type vaccinia, or not infected at all. The results showed that only the LCL that were autologous to the HLA A*0201 allele were being recognized and killed by the 3-3F4 T cell line. It was also established that 3-3F4 is of the CD8$^+$ T cell subset, characteristic of CTL which recognize Class I restricted peptides. Whether the cell line was monoclonal was tested by carrying out PCR repertoire analysis using a series of 26 human V$\beta$ gene segment primers. Only one of 26 primers gave a significant signal, the V$\beta$13.1 primer, thereby demonstrating the apparent monoclonality of the 3-3F4 T cell clone.

To identify the precise epitope or peptide recognized by the T cell clone 3-3F4, a series of vaccinia truncations that deleted the pp65 protein from the carboxyl towards the amino terminus was used. A CRA was conducted utilizing autologous and HLA mismatched LCL targets infected with vaccinia viruses expressing truncation products of the pp65 protein. This experiment localized a region between amino acids 377 and 561 that was necessary for killing of targets. Utilizing a small subset of amino terminal deletions, the region necessary for killing was further localized between amino acids 477 and 561. Utilizing an indirect killing assay, a monkey kidney cell line was transfected with the molecular HLA allele HLA A*0201 and portions of the pp65 gene to localize the region to a fragment containing amino acids 452–561. The final determination of the peptide sequence that corresponds to the sequence bound by HLA A*0201, and is recognized by T cell clone 3-3F4 was done by producing 9–10 amino acid peptides on a Synergy (Applied Biosystems Model 432) peptide synthesis machine. Using published information, a series of candidate sequences were determined that had significant characteristics of an HLA A*0201 binding sequence, and were located in the region between amino acid 452–561. These were:

TABLE 1

| Amino Acid Sequence of Peptide | Position Number | Motif | Score* |
|---|---|---|---|
| ILARNLVPMV (SEQ ID NO: 26) | 491 | A*0201 | 67 |
| ELEGVWQPA (SEQ ID NO: 27) | 526 | A*0201 | 59 |
| RIFAELEGV (SEQ ID NO: 28) | 522 | A*0201 | 55 |
| NLVPMVATV (SEQ ID NO: 1) | 495 | A*0201 | 63 |

*(adapted from J. D'Amaro et. al., "A computer program for predicting possible cytitoxic epitopes based on HLA Class I peptide binding motifs," Human Immunology 43:13–18 (1995)).

Only one of these peptides (referred to as "the 495 peptide" or as "pp65$_{495-503}$") (SEQ ID NO:1) proved capable of priming the autologous LCL to be recognized and killed by the CD8$^+$ CTL 3-3F4. Other 9–10 amino acid peptides from pp65 that also followed the HLA A*0201 motif were tested in the CRA. None showed any activity. All peptides were examined for purity by HPLC on a Vydac $C_{18}$ column using acetonitrile/TFA as the moving phase. They were 70–80% pure or greater on average, and were used as dilutions from 0.1% acetic acid solution.

EXAMPLE 5

Use of the 495 Peptide to Induce Cell Lysis

Serial dilutions of the 495 peptide showed no change in activity between 10 $\mu$M and 0.01 $\mu$M in priming autologous LCL for killing by T cell clone 3-3F4 in a CRA. Half-maximal lysis occurred at close to 0.5 nM peptide. The peptide-transporter deficient cell line T2 (D. B. Crumpacker et al., *J. Immunol.* 148:3004–3011 (1992)), which is HLA A*0201 positive, also was used to test the lower limits of sensitivity of the 3-3F4 T cell clone for recognition of the peptide in a CRA. It was found that as little as 0.1 nM peptide caused maximal lysis of T2 cells, equivalent to the condition with 10 nM peptide. These experiments demonstrate that this minimal cytotoxic epitope is a strong binder to the HLA A*0201 allele.

The 495 peptide depicted in Table 1 was prepared on a Synergy (Applied Biosystems Model 432) peptide synthesis machine. Dermal fibroblasts were primed with the peptide, then loaded with chromium-51 by incubation with 10 μM of the 495 peptide for 2 hours at 37° C., and for the final hour with chromium-51. The peptide and chromium-51 were washed out of the medium.

T cell clone 3-3F4 (CD8+ CTL), derived from an HCMV seropositive individual (HLA A*0201 positive) was capable of recognizing the HCMV-infected fibroblasts as well as the peptide-primed fibroblasts in a CRA. Uninfected and unprimed fibroblasts were not recognized or killed by the T cell clone. In addition, an HLA-mismatched fibroblast line without the HLA A*0201 allele found on the donor fibroblasts was not recognized or killed by the T cell clone when it was either infected by HCMV or primed with the 495 peptide. Thus, the 495 peptide of the present invention can serve as a substitute for the whole HCMV virus, causing normal T cells to recognize and kill fibroblasts as effectively or better than if they were infected with HCMV.

EXAMPLE 6

Generation of TNF-α by T Cell Clones

TNF-α is a T cell lymphokine that is cytotoxic for many cell types and may contribute to the in vivo immune response mounted against an HCMV infection. Cells of the 3-3F4 T cell clone were incubated with autologous fibroblasts pre-incubated with either whole HCMV virions or primed with the 495 peptide of Table 1. Twenty four hours later, supernatants from the co-incubated cells were applied to an indicator cell line in a bioassay as described above. The indicator cell line, a WEHI derivative, is sensitive to the cytotoxic action of TNF-α at the picomolar level.

Peptide-primed fibroblasts induced the production of as great or greater levels of TNF-α from T cell clone 3-3F4 as were the HCMV-infected fibroblasts. The peptide of SEQ ID NO:1 did not induce TNF-α production by either autologous fibroblasts incubated without T cells or non-HLA-A*0201 expressing fibroblasts incubated with the T cell clone.

EXAMPLE 7

Peptide SEQ ID NO:1 can Induce CTL from PBL of HCMV Seropositive Individuals

PBL from HCMV-seropositive individuals were plated onto SEQ ID NO:1 peptide-primed autologous fibroblasts or incubated with irradiated autologous PBL sensitized with SEQ ID NO:1 peptide for seven days. The once-stimulated PBL were re-stimulated in a similar manner, either with or without depletion of CD4 T cells. After two weeks, a chromium release assay was performed using as targets either peptide-primed, CMV-infected, or untreated autologous fibroblasts. CD8+ T cells lysed significant percentages of the peptide-primed and HCMV-infected fibroblasts or EBVLCL primed with SEQ ID NO:1, but not untreated cells. No autologous fibroblast targets were lysed by CD4-depleted PBL from freshly drawn blood under the same conditions. Experiments were repeated with T cells from 15 healthy adult volunteers. In all but one case, donor possessing a matching HLA allele had T cells which responded to SEQ ID NO:1. Similar experiments were conducted with HIV patients, without in vitro stimulation of the T cells. The majority of HIV positive donors with a matching HLA allele also possessed T cell clones which could recognize autologous EBVLCL primed with SEQ ID NO:1.

EXAMPLE 8

Human Cell Lines which Express HLA A2, with Molecular Subtypes other than A*0201, are Sensitized to Lysis by the 495 Peptide Twelve cell lines were subjected to chromium release assays in which they were pulsed with the 495 peptide (pp65$_{495-503}$) nonamer, loaded with chromium-51, and incubated with two different HLA A*0201 restricted CTL which recognize the 495 peptide and HCMV. The specific cytotoxicity was calculated and is shown in tabular form below for the 1 μM and 1 nM concentrations of the 495 peptide. A plus sign (+) represents cytotoxicity greater than 30%, a plus/minus sign (+/−) represents cytotoxicity between 5% and 30%, and a minus sign (−) represents cytotoxicity less than 15%.

TABLE 2

| HLA-A2 Subtype | CTL 3-3F4 | | CTL VB-57 | |
| --- | --- | --- | --- | --- |
|  | 1 μM | 1 nM | 1 μM | 1 nM |
| A*0201 | + | + | + | + |
| A*0202 | + | − | + | − |
| A*0203 | + | − | − | − |
| A*0204 | + | + | + | + |
| A*0205 | + | − | + | + |
| A*0206 | + | + | + | + |
| A*0207 | + | + | + | + |
| A*0209 | + | − | + | − |
| A*0210 | + | + | + | + |
| A*0211 | + | − | + | +/− |
| A*0217 | + | − | + | + |

The data showed that all tested subtypes functionally bound the 495 peptide at 1 μM, and the cell lines were lysed by the HCMV and pp65 specific CTL. These data also showed that the cell line subtypes shown here were capable of being sensitized for lysis by the 495 peptide. The data also indicate that cells from individuals who carry these subtypes can be sensitized by the peptide for CTL recognition and lysis, albeit at a higher concentration in most cases than what was found for HLA A*0201. Thus, individuals who carry any of these HLA A2 subtypes can respond to the 495 peptide as a vaccine.

EXAMPLE 9

Animal Studies using the 495 Peptide (SEQ ID NO:1)

A transgenic mouse model lacking prior HCMV exposure, the HLA A2.1 mouse (E. J. Bernhard et al., *J. Exp. Med.* 168:1157–1162 (1988)), was employed to test whether the 495 peptide could stimulate CTLs lacking prior virus exposure and function as a vaccine. These experiments involved in vitro analysis using mouse and human cell targets, either infected with viruses or primed with the peptide of SEQ ID NO:1 or a non-specific control peptide.

Three mice were immunized subcutaneously at the base of the tail with 50 μg of the 495 peptide (pp65$_{495-503}$) or peptide P53$_{149-157}$ from p53 (M. Theobald et al., *Proc. Natl. Acad. Sci. U.S.A.* 92:11993–11997 (1995)) together with 20 μg of the polyclonal helper T lymphocyte (HTL) peptide (PADRE; SEQ ID NO:29) (J. Alexander et al., *Immunity.* 1:751–761 (1994)) emulsified in IFA (Incomplete Freund's Adjuvant). After twelve days, spleens were removed from immunized mice, a splenic suspension was made, and the effector cells were restimulated for one week using P53$_{149-}$ 157 or pp65$_{495-503}$ peptide sensitized syngeneic lipopolysaccharide-treated splenic blast cells (P. A. Wentworth et al., *Eur. J. Immunol.* 26:97–101 (1996)). Thereafter, for subsequent in vitro stimulations, the stimulator cells were Jurkat A2.1 cells, prepared by mild acid treatment and subsequent loading of peptides (Z. Yu et al., *Journal of Surgical Research* 69:337–343 (1997)). After two in vitro restimulation cycles, the murine splenic effector population was tested for recognition of P53$_{149-157}$ or pp65$_{495-503}$ peptide loaded T2 cells. There was substantial recognition of pp65$_{495-503}$ or P53$_{149-157}$ peptide in mice that had been appropriately immunized, without recognition of the non-immunizing peptide.

It was also demonstrated that murine splenic effectors recognize endogenously processed pp65 in a chromium release assay with human HLA A*0201 EBVLCL targets infected with pp65Vac (D. J. Diamond et al., *Blood* 90 (5):1751–1767 (1997)). Further proof that the pp65$_{495-503}$ peptide causes recognition of virus-infected cells came from a chromium release assay using HCMV-infected human fibroblasts as targets, and murine CTL derived from the pp65$_{495-503}$ peptide stimulation as the effector population. HLA A*0201 fibroblasts infected with HCMV were capable of lysis by the CTL, whereas both uninfected and mismatched fibroblasts were not recognized (D. J. Diamond et al. *Blood* 90 (5):1751–1767 (1997)). Taken together, these results clearly showed that the splenic effector population from a primary immunization with pp65$_{495-503}$ are recognized endogenously processed pp65 and HCMV in an HLA A*0201 restricted manner.

An additional study demonstrated that the 495 peptide induced a long-lived immune response in animals. Twelve mice were simultaneously immunized with the 495 peptide (SEQ ID NO:1)+PADRE (AKXVAAWTLKAAA; SEQ ID NO:29)+IFA, and two additional control mice were immunized with PADRE+IFA alone. At two weeks, 6 weeks, 10 weeks and 14 weeks after the immunization, the spleens from two immunized mice were analyzed for immunity against the 495 peptide or a control peptide from human p53 (P53$_{149-157}$) In addition, at two and six weeks, mice immunized without the 495 peptide also were sacrificed and their spleen cells analyzed for immune responses against the 495 peptide or the human p53 peptide. Percent specific cytotoxicity (cytotoxicity of 495 peptide targets—cytotoxicity of p53 targets) was still at a level of 40% after 14 weeks, whereas naive animals did not show any specific cytotoxicity above 5%. This compared well with recent results from immunizing human volunteers with the Theradigm™ lipopeptide (B. Livingston et al., *J. Immunol.* 159:1383–1392 (1997)) in which there was an average maintenance of 60% of the initial response 38 weeks after the final of four immunizations over an eighteen week period.

EXAMPLE 10

Lipidated Peptides Incorporating pp65$_{495-503}$ (SEQ ID NO:1) as IFA-Adjuvant Independent Vaccines in Animals Although the use of adjuvants to enhance immunogenicity is a common strategy in animal studies, there are important limitations concerning their use in humans. Therefore, one embodiment of the present invention involves peptides which incorporate lipid molecules. This strategy has been efficacious in both animal (K. Deres et al., *Nature* 342:561–564 (1989)) and human clinical studies (A. Vitiello et al., *J. Clin. Invest.* 95:341–349 (1995)) to avoid having to use adjuvants.

Either one or two palmitic acid moieties were attached to the amino terminus of the 495 peptide, and a series of immunization studies were conducted in the transgenic HLA A2.1 mouse. The primary structure of the directly lipidated peptides is shown in Table 3.

TABLE 3

Primary Structure of Peptides Used to Immunize HLA A2.1 Transgenic Mice

| Lipid Molecule(s) | Adaptor Sequence | Epitope Sequence (SEQ ID NO: 1) | Carboxyl Terminus | SEQ ID NO: |
|---|---|---|---|---|
| 0 | -KSS- | -NLVPMVATV- | OH | 30 |
| 1 PALMITIC ACID | -KSS- | -NLVPMVATV- | OH | 31 |
| 2 PALMITIC ACID | -KSS- | -NLVPMVATV- | OH | 32 |

Table 3. Peptides were synthesized on the ABI 432 (Applied Biosystems), and purified and analyzed as described (D. J. Diamond et al., *Blood* 90 (5):1751–1767 (1997)). Palmitic acid (Aldrich) was dissolved in dimethylformamide, and automatically coupled to the amino terminal lysine. The amino terminal lysine of the monolipidated form of the peptide was protected by two protecting groups, Fmoc and Boc. Only the Fmoc group is cleaved during synthesis to allow for a single lipid moiety to be added. For the dilipidated form, the amino terminal lysine was protected with two Fmoc groups, therefore allowing two lipid moieties to be added. Peptides also may be lipidated at other locations by methods well known in the art and are contemplated for use here.

Figure 2:
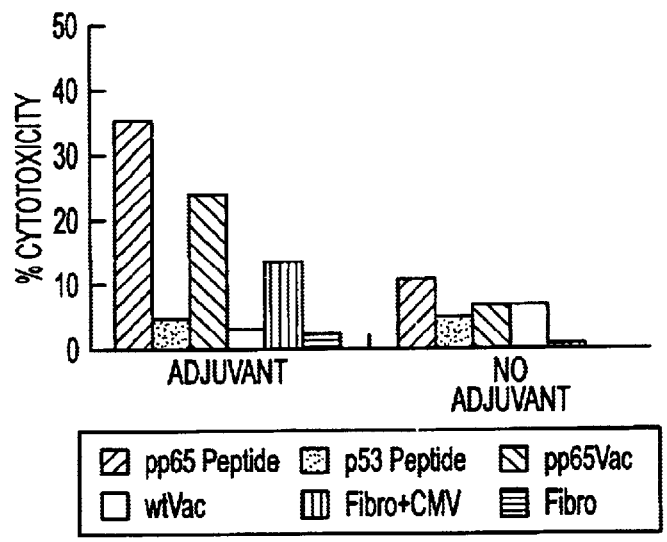
FIG. 2 shows the cytotoxic response elicited by monolipidated peptides.
Figure 3:
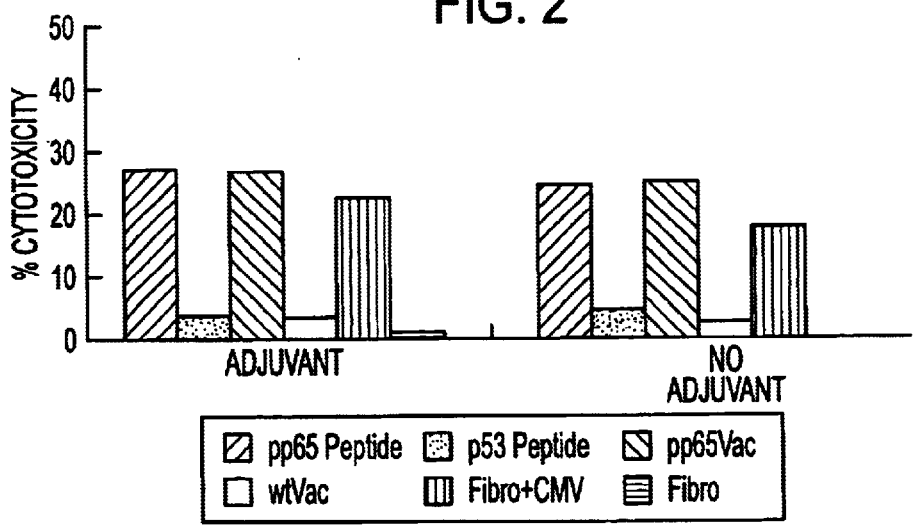
FIG. 3 shows the cytotoxic response elicited by dilipidated peptides.

Separate mice were immunized with unmodified pp65$_{495-503}$, and either the monolipidated or dilipidated forms of the peptide together with the PADRE epitope. Because it has been previously shown that lipidated peptides will stimulate immunity without co-administration of Freund's adjuvant (H. Schild et al., *Eur. J. Immunol.* 21:2649–2654 (1991)), immunization of mice with and without emulsifying the peptides in IFA was compared. In a procedure similar to the procedure described in Example 9 above, twelve days post inoculation the mice were splenectomized and the spleen cell population was restimulated twice in vitro. The splenic effectors were then tested in a chromium release assay with peptide-loaded T2 cells, EBVLCL targets infected with pp65Vac, and HCMV-infected fibroblasts (D. J. Diamond et al., *Blood* 90 (5):1751–1767 (1997)). The results demonstrate that the lipidated form of the 495 peptide, without emulsification in adjuvant, induces an immune response capable of recognizing endogenously-processed pp65 and HCMV-infected human cells. The monolipidated form appeared to induce a weaker immune response (compare with and without IFA), whereas the unmodified free peptide had no activity unless emulsified in IFA. (See FIGS. 1–3)

These data illustrate an advantageous immunization/vaccination procedure for use in warm blooded animals, including humans. The procedure entails the mixture of two peptides in an aqueous solvent system (the lipidated 495 peptide plus either PADRE or the 830–843 amino acid tetanus peptide, Table 3). The mixture is administered subcutaneously or via another acceptable and efficacious route to either HCMV seropositive or seronegative subjects. An additional set of booster injections may be employed to enhance the immunity induced by primary vaccination.

EXAMPLE 11

Formulation of Lipidated Vaccines

The 495 peptide and functional sequence variants thereof can be formulated as a vaccine as a lipidated peptide with a covalent HTL epitope. The HTL epitope can be any peptide that has broad reactivity to human MHC class II to stimulate a classic helper response. Such molecules include but are not limited to amino acids 830–843 from tetanus toxin (P. Panina-Bordignon et al., *Eur. J. Immun.* 19:2237–2242 (1989)), HTL epitopes from HIV envelope protein (J. A. Berzofsky et al., *J. Clin. Invest.* 88:876–884 (1991)), or a synthetic version (PADRE) predicted from known anchor residues (J. Alexander et al., *Immunity* 1:751–761 (1994)).

The lipidation of the HTL+CTL epitope preferably is performed on the amino terminus of the HTL epitope, with the HTL epitope being amino terminal to the CTL epitope. Suitable lipid moieties are known and described in the literature. (H. Schild et al., *Eur. J. Immunol.* 21:2649–2654 (1991); A. Vitiello et al., *J. Clin. Invest.* 95:341–349 (1995); K. Deres et al., *Nature* 342:561–564 (1989)). Alternatively, the CTL epitope can be lipidated at its amino terminus, followed by the HTL epitope, or the lipid can be found at the carboxyl terminus followed by either the CTL or HTL epitope(s). A three amino acid spacer or any other spacer can be inserted between the HTL and CTL epitope, or the epitopes can be fused directly in frame. Alternatively the CTL epitope lipidated on its amino terminus can be administered together with the HTL epitope, without covalent attachment. The vaccine epitopes, regardless of primary structure, may be injected s.c. into the forearm in a standard formulation buffer (e.g., PBS or PBS/10% DMSO or higher concentration/0.01% triflouroacetic acid or other acid or alcohol of the same or different concentration) once. Three to six weeks later, a booster injection of the same material may be administered. Multiple booster injections spaced three to six weeks apart can be subsequently administered, if necessary.

This injection series can be administered to a patient or at-risk individual, or to the donor of a bone marrow transplant, who is either positive or negative for the virus. Illustrative examples of lipidated vaccine peptides include, for example:

TABLE 4

| N-terminal | C-terminal |
| --- | --- |
| (Pam)$_2$-KSS*QYIKANSKFIGITE*<u>AAA</u>NLVPMVATV | (SEQ ID NO:33) |
| (Pam)$_3$-CSS*QYIKANSKFIGITE*<u>AAA</u>NLVPMVATV | (SEQ ID NO:34) |
| (Pam)$_2$-KSS*AKXVAAWTLKAAA*<u>GGG</u>NLVPMVATV | (SEQ ID NO:35) |
| (Pam)$_3$-CSS*AKXVAAWTLKAAA*<u>GGG</u>NLVPMVATV | (SEQ ID NO:36) | wherein X is cyclohexylalanine or phenylalanine. As is the case throughout, all amino acids are represented by their universal one-letter code. "Pam" is palmitic acid. The three-A or -G spacer (underlined) can be interchanged among vaccine peptides. The format of the peptides shown above can be described (from the amino terminus) as: lipid-K/CSS—HTL epitope (italics)—amino acid spacer (underlined)—CTL epitope. The positions of the CTL and HTL epitopes may be interchanged. The CTL epitope (or a functional sequence variant thereof) may be further modified by adding a leader sequence and/or the amino acids KDEL can be appended to the carboxyl terminus to enhance retention and targeting into the endoplasmic reticulum. Palmitic acid or any suitable lipid may be used, including but not limited to stearic acid, myristic acid, lauric acid, capric acid and decanoic acid.

EXAMPLE 12

Use of Combined HTL and CTL Epitope, Lipidated at the Amino Terminus, as a Single Component Vaccine in Transgenic Mouse Studies Two further molecules, each containing lipid, HTL and CTL epitopes, were constructed and tested in mice:

TABLE 5

| N-terminal | C-terminal |
| --- | --- |
| A. | |
| (Pam)$_2$-KSSAKXVAAWTLKAAANLVPMVATV | (SEQ ID NO:37) |
| B. | |
| (Pam)$_2$-KSSISQAVHAAHAEINE<u>AAA</u>NLVPMVATV | (SEQ ID NO:38) |

Nomenclature for Table 5 can be found in the legend to Table 4.

Molecule A (SEQ ID NO:37) is a vaccine that has the capability of working in mice and humans, whereas molecule B (SEQ ID NO:38) should only be functional in mice. One hundred nanomoles of each of these vaccine peptides in 25% dimethysulfoxide in phosphate buffered saline with 2.5% hexafluoroisopropanol were injected s.c. into separate transgenic HLA A2.1 mice.

The methods referred to in Examples 9 and 10 were used to derive spleen cell populations containing cells which were specific against pp65 and HCMV. The spleen cells from immunized mice were tested for recognition and cytolysis against specific and non-specific peptide-sensitized targets, HCMV infected and non-infected HLA A*0201 and HLA-mismatched fibroblast targets. The 495 pp65$_{495-503}$ peptide sensitized targets were effectively lysed, whereas targets sensitized with a peptide derived from another protein (human p53) which binds to HLA A*0201 (P53$_{149-157}$) were ineffective. In addition, and importantly, HCMV-infected HLA A*0201 fibroblasts were effectively lysed, but uninfected fibroblasts or those which are HLA-mismatched were not recognized or lysed, regardless of HCMV infection. These results were obtained with both molecules A and B, although molecule A was the more potent of the two. However, a second immunization (booster) of mice immunized with Vaccine A at lesser amounts of 50 nmole resulted in a detectable immune response when a single immunization was not effective (Table 5). This stimulative effect of the booster is in agreement with B. Livingston et al., *J. Immunol.* 159:1383–1392 (1997)). These data showed that the single molecule form of the vaccine functions to stimulate HCMV immunity in an animal model without any added molecules or adjuvant other than the vaccine molecules A or B (Table 4) in liquid vehicle (e.g., PBS/DMSO/HFIP). The data also demonstrated that the vaccine is capable of stimulating a de novo immune response to HCMV in a HCMV-naive mouse.

EXAMPLE 13

Additional HCMV pp65 CTL Epitopes Specific for HLA A and B Alleles

There are over 100 known HLA Class I alleles of the A and B genes. (J. G. Bodmer et al., *Tissue Antigens* 49:297–321 (1997)). Using a combination of predictive algorithms and truncation analysis, additional peptides from pp65 that sensitize both autologous and allogeneic cells to be lysed by MHC-restricted human CTL were identified. As discussed in Example 1, the CTL arise from HCMV seropositive humans; therefore, the defined epitopes from pp65 were those used by humans to suppress endogenous HCMV reactivation or viremia. To define CTL reactive against HCMV pp65 in combination with specific HLA alleles, individual cloned CTL lines were tested for recognition of EBVLCL infected with pp65vac which contained one of the HLA A or B alleles found in the individual whose blood was used to derive the CTL. In cases where at least one HLA allele is shared between the EBVLCL targets and the CTL, sensitization for recognition and lysis was observed. This experiment was repeated with at least three independent cell lines containing the restricting allele. Table 6 shows the pp65 epitopes, their HLA restriction, the number of independent cell lines of the same restriction which were sensitized, and the method(s) of delineation of the epitopes.

TABLE 6

| HLA A or B Allele Specificity | Number of Test Cell Lines | Method(s) of Determination | Minimal Cytotoxic Epitope Sequence |
|---|---|---|---|
| HLA A*0101 and subtypes | 3 | A, B, C, D, E | YSEHPTFTSQY (SEQ ID NO: 3) |
| HLA A*6801 and subtypes | 3 | A, B, D, E | FVFPTKDVALR (SEQ ID NO: 5) |
| HLA B7 and subtypes | 5 | A, B, D, E | TPRVTGGGAM (SEQ ID NO: 7) |
| HLA B*3502, 04, 06 and subtypes | 3 | A, B, C, D, E | FPTKDVAL (SEQ ID NO: 9) |
| HLA B7 and subtypes | 5 | A, B, C, E | RPHERNGFTVL (SEQ ID NO: 10) |
| HLA A*1101 and subtypes | 5 | A, B, C, E | SVLGPISGHVLK (SEQ ID NO: 11) |
| HLA A*0201 and subtypes | 5 | A, B, C, D, E | NLVPMVATV (SEQ ID NO: 1) |
| HLA B*3801/2 | 3 | A, B, E | PTFTSQYRIQGKL (SEQ ID NO: 12) |
| HLA B*44XX | 2 | D | EFFWDANDIY (SEQ ID NO: 13) |
| HLA A*2402 | 4 | A, B, E | FTSQYRIQGKL (SEQ ID NO: 14) |

Methods of Determination: (A) HLA Restriction using single HLA allele matched cell lines; (B) pp65 truncations in vaccinia viruses; (C) pp65 truncations in plasmids with detection of activity using TNF-α assay; (D) matching of amino acid residues using published motifs; (E) functional analysis using ordered overlapping peptides.

EXAMPLE 14

Vaccine Molecules Comprised of More than One CTL Epitope

In accordance with the procedures described herein, vaccines containing a combination of pp150 and/or pp65 epitopes, specific for the same or different HLA Class I restriction elements, were prepared. For vaccination of humans there is no necessity for each epitope to have the same MHC restriction. A vaccine molecule which targets two or more MHC restriction elements may be preferred because it allows the production of fewer vaccine molecules, and still ensures that most HLA alleles were targeted in a polymorphic population. Peptides with CTL epitopes which are restricted by frequently expressed HLA alleles (see Tables 1 and 6) are preferred, and polypeptide vaccines containing epitopes from both the pp65 and pp150 proteins, as well as an HTL epitope, are especially preferred for human vaccination against HCMV. The HLA alleles shown in Tables 1 and 6 are a subset of possible HLA A, B, and C CTL epitopes to be included in a multiple CTL epitope vaccine molecule. The inclusion of multiple CTL epitopes and an HTL epitope will lengthen the peptides (in the range of 40–50 amino acids). Alternatively, HCMV polypeptide vaccines may be prepared without a covalently attached HTL epitope by using multiple CTL epitopes with a spacer of three alanine residues or another combination of amino acids between each epitope, and two palmitic acid-lysyl amides at the N-terminus, as shown in Table 3.

The hydrophobicity of the sequence is an important factor. To reduce hydrophobicity, lipid modification may be omitted. In addition, multiple HLA epitopes may be formulated into a cocktail vaccine. Preferably, each individual CTL epitope in the mixture would be fused to a CD4 T-cell epitope as described above. Thus, the cocktail vaccine could be formulated to contain epitopes sufficient to cover about 75% to about 90% of a multi-ethnic population using the sequences shown in Table 6.

EXAMPLE 15

Immunization of BMT Patients

A therapeutically active form of an antigenic peptide according to the present invention is administered to an HCMV-seropositive bone marrow transplant donor at a sufficient time (six to eight weeks, for example) in single or multiple doses separated by a given number of days or weeks prior to bone marrow transplant to enable the development of an anti-HCMV cellular immune response. The antigenic peptide can be formulated in per se known manners (for example, as a lipidated peptide, optionally in combination with a helper peptide and/or an adjuvant) and will be administered, preferably, in multiple doses. Peptides in which the helper peptide and antigenic peptide are linked together in one sequence, for example are suitable for this purpose.

An additional vaccine regimen consists of priming a donor with a modified Vaccinia Ankara (MVA) containing a polynucleotide viral vaccine, for example, full-length pp65, pp65 fragments or one or more of the CTL epitopes shown in Table 6, followed by boosting with a peptide vaccine as described in Examples 12 and 14. Those of skill in the art are fully able to devise schemes for vaccination using various combinations of peptide and virus administration, and these variations are contemplated for use with the present invention. If an unmanipulated BMT graft will be given to the recipient, such a graft will contain 25% or more of mature T cells. The T cells confer active immunity to he BMT recipient patient. Alternatively, when a T-cell depleted BMT graft is to be employed, an aliquot of T cells from the immunized donor can be administered to the patient following (for example, approximately 21 to 35 days) BMT to provide the recipient patient with HCMV immunity.

EXAMPLE 16

In Vitro Assay for HCMV Infected Cells

The peptides of the present invention are used in an in vitro assay to detect the presence or absence of HCMV-infected cells obtained, from a patient whose HCMV status (infected or uninfected) is unknown. T lymphocytes obtained from the patient are incubated with antigen presenting cells primed with a peptide of the present invention. The activation of CTL or CTLP reveals that the patient was infected with HCMV.

EXAMPLE 17

Induction of Immune Response by Vaccination of Transgenic Mice with Unlipidated Peptide Two HLA-A2.1k$^b$ transgenic mice were inoculated with 100 nmoles of the A2 HCMV pp65 peptide NLVPMVATV (SEQ ID NO:1) in 10% DMSO, 0.1% acetic acid with 20 μg of the T-helper peptide, PADRE (AKXVAAWTLKAAA where X signifies cyclohexylalanine; SEQ ID NO:29), emulsified in a 1:1 ratio with incomplete Freund's adjuvant by sonication for 15–30 seconds. To account for loss during transfer, 300 μL or more excess emulsified vaccine over that required for injections was prepared. The peptide vaccine (100 μL total volume emulsified preparation above) was injected subcutaneously at the base of the tail, 50 μL on each side, avoiding the lateral tail veins. Positive control animals were injected in the same manner with the unrelated HLA-A2.1 restricted hu $p53_{1147-157}$ peptide and PADRE. A booster was administered seven days later. One week after the booster immunization, splenocytes were harvested, cultured, and stimulated in vitro. For cultivation, the cells were isolated from the spleens and suspended in 40 mL medium and counted. Erythrocytes were omitted from the counting. The cells were then brought to a concentration of three million cells per milliliter in medium containing 20% Rat-Stim (Collaborative Biomedical Cat #40115, Waltham, Mass.), and plated at 1 mL/well in 24-well plates. To stimulate the cells, 1 mL suspended antigen-presenting cells (at a ratio of 3 immunized splenocytes to 1 antigen presenting cell) were added to the culture. The cells were incubated at 37° C. for seven days. Fresh medium was added as necessary. Stimulations were performed every seven days after plating by addition of 1 mL suspended antigen presenting cells as above.

Antigen presenting cells were prepared as follows. For each immunized group of mice, the spleens of three mice were removed aseptically and suspended at a concentration of 1.0–1.5×10⁶ cells per mL in RPMI with 10% FCS containing 25 μg/mL LPS and 7 μg/mL dextran sulfate for three days at 37° C. in 5% $CO_2$. The cells then were collected, sedimented, resuspended in serum-free medium and counted. Cells were dispensed in volumes containing 25 million cells into 15 mL conical centrifuge tubes and gently sedimented at 1200 rpm for six minutes. The supernatant was aspirated, leaving 100 μL in the tube. Peptide (SEQ ID NO:1) (100 μM) was added to the tube, mixed well and incubated four hours at 37° C. and 5% $CO_2$. The cells were resuspended in 2 mL complete medium (RPMI 1640 containing 10–12 mM HEPES, 2 mM L-glutamine, 100 U/mL penicillin, 100 U/mL streptomycin, 50 μM β-mercaptoethanol and 10% heat-inactivated fetal calf serum) per tube and concentrated in sterile PBS. The cells were then irradiated with 2500 rads from a $^{137}Cs$ source and then brought to a concentration of 1 million cells per mL in complete medium for use in stimulating the immunized splenocytes.

Six to seven days after in vitro stimulation, immunized splenocytes (effector cells) were collected and the cytotoxic activity of the cells was assayed against peptide-loaded or untreated target cells using a $^{51}Cr$ release assay. A bulk cell line specific for $pp65_{495-503}$ (SEQ ID NO:1) derived from HLA-A2.1 $k^b$ immunized mice and stimulated weekly with the peptide was used as a positive control line. T2 cells were used as targets, either unloaded or loaded with either the peptide of SEQ ID NO:1 or a human control peptide derived from p53. See Example 9. To prepare the targets for the chromium release assay, T2 cells in the log phase of growth were sedimented and resuspended in 10 mL LCL medium (RPMI 1640 containing 1% HEPES, 10% fetal calf serum, 2% L-glutamine and antibiotics) for each of unloaded or loaded groups. The cells were counted, resedimented, and suspended in 1 mL or less LCL medium. Cells were either unloaded or were loaded with 10 μl of a 5 mM solution of the appropriate peptide as described above for stimulating antigen-presenting cells. All cells were loaded with 20 μl $^{51}Cr$ stock solution containing 10 mCi/mL $Na_2^{51}CrO_4$. The tubes of cells then were incubated in a 37° C. waterbath for 45–60 minutes, shaking gently every 15 minutes. The cells then were washed three times in 10 mL RPMI and resuspended in 1 mL LCL medium. The target cells were recounted and suspended in appropriate volumes of LCL medium to achieve 20,000 cells/mL, and then placed in a 96-well plate at 100 μL per well.

Effector cells (immunized splenocytes) cells were brought to 2 million cells per mL in RPMI containing 10% FCS and added to the wells containing target cells at different Effector:Target ratios as indicated in FIG. 4. Medium alone (100 μL) was added to negative control wells to measure spontaneous release of $^{51}Cr$, and medium containing 2% sodium dodecyl sulfate (100 μL) was added to positive control wells to measure total possible release of $^{51}Cr$. The plate was subjected to 600 rpm for six minutes with no break in a Sorvall RT7 centrifuge (Kendro Laboratory Products; Newtown, Conn.) and incubated for four hours at 37° C. and 5% $CO_2$, then resedimented for six minutes at 1200 rpm. The supernatants then were harvested and the radioactivity measured with a Packard Cobra II gamma counter (Packard Instruments; Meriden, Conn.). Specific CTL activity was calculated as follows:

% specific release=100×(experimental release−spontaneous release) (total release−spontaneous release)

Figure 4A:
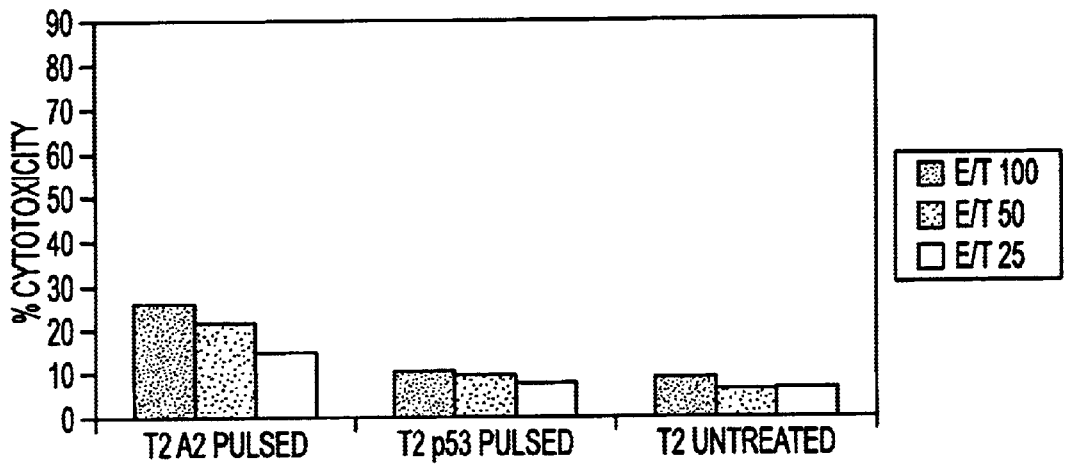
FIG. 4 is bar graphs showing cytotoxicity of antigen presenting cells by immunized splenocytes after one (A), two (B) or four (C) in vitro stimulations.
Figure 4B:
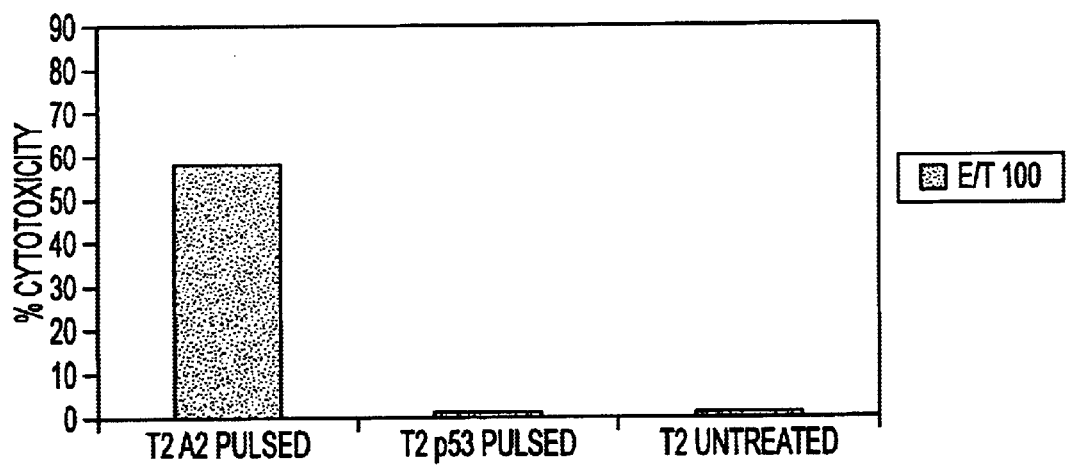
Figure 4C:
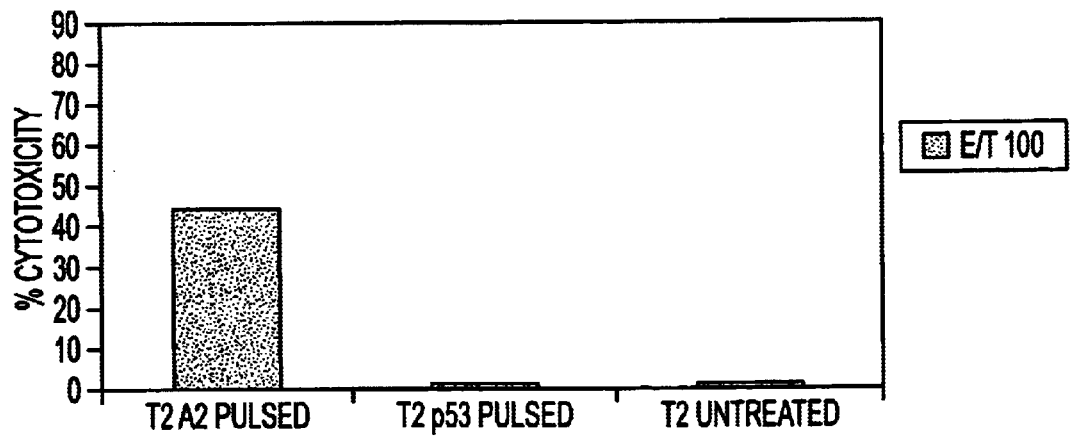

Experiments in which spontaneous release was 30% or greater of maximum total release were discarded. FIG. 4A shows results after one in vitro stimulation, FIG. 4B shows results after two in vitro stimulations, and FIG. 4C shows results after four in vitro stimulations. In this figure and those which follow, "T2 A2 pulsed" indicates cells presenting the peptide of SEQ ID NO:1, "T2 p53 pulsed" indicates cells presenting the human control peptide $P53_{149-157}$. The data showed that the vaccination with the inventive peptide vaccine did result in specific CTLs which could recognize and kill appropriate targets. Results improved with a second in vitro stimulation.

EXAMPLE 18

Comparison of Lipidated Vaccine Formulations

Figure 5B:
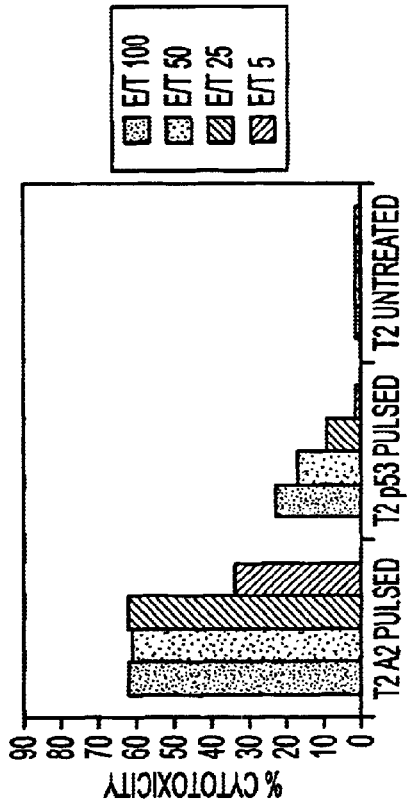
FIG. 5 presents the results of chromium release assays for cells immunized with SEQ ID NO:37.
Figure 5D:
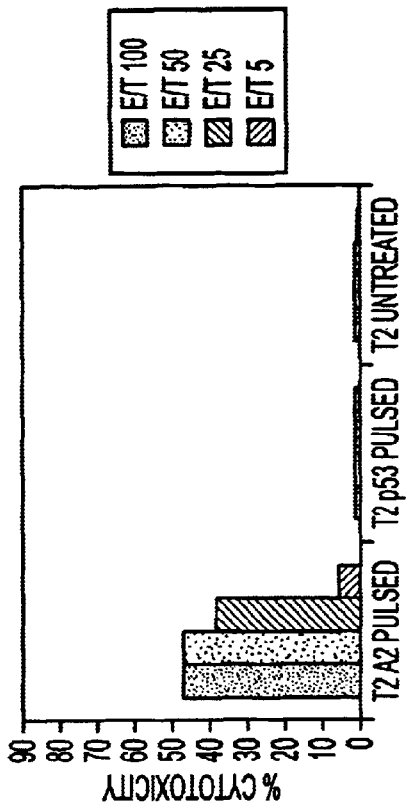
Figure 5A:
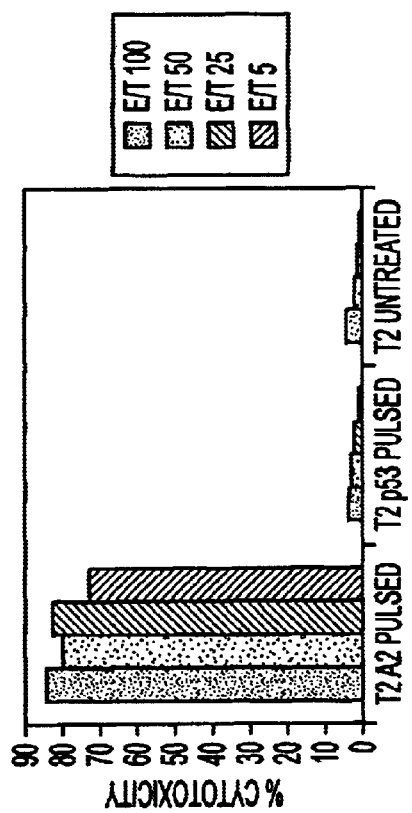
Figure 5C:
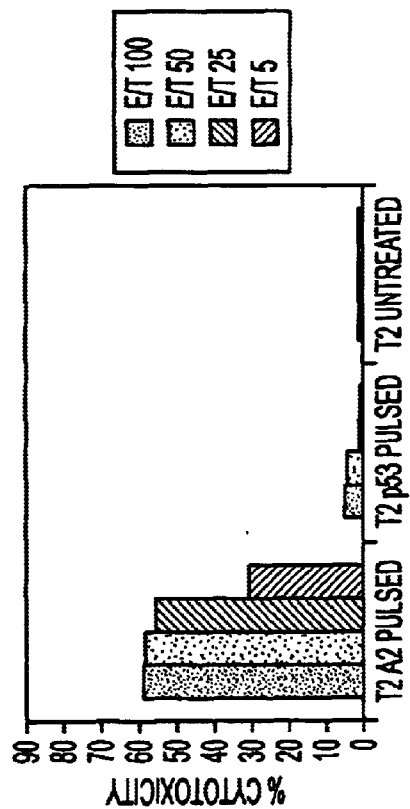
Figure 6A:
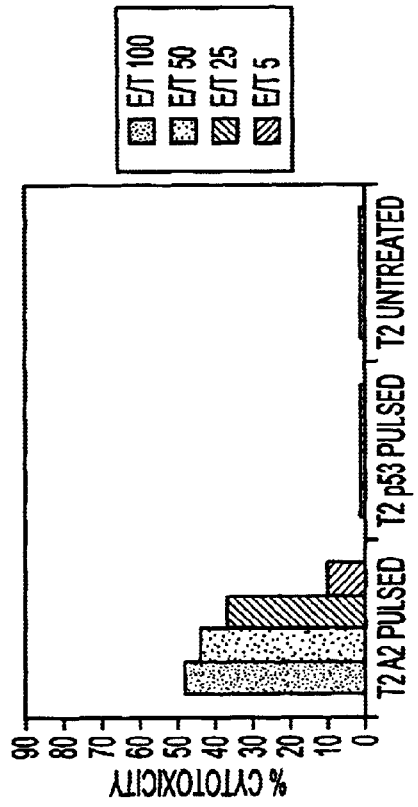
FIG. 6 presents the results of chromium release assays for cells immunized with SEQ ID NO:37.
Figure 6B:
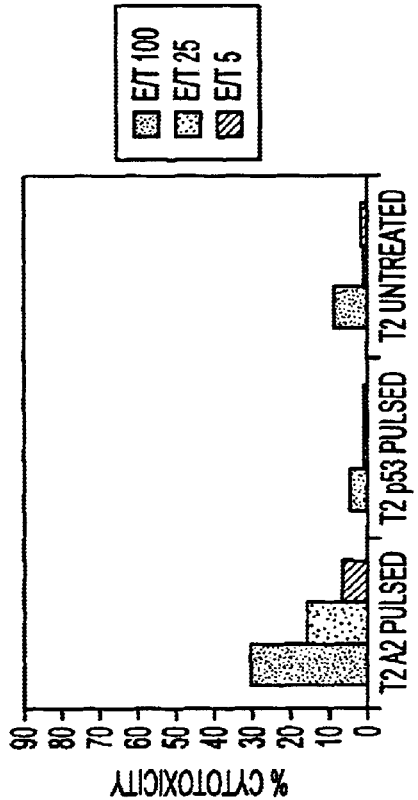
Figure 6C:
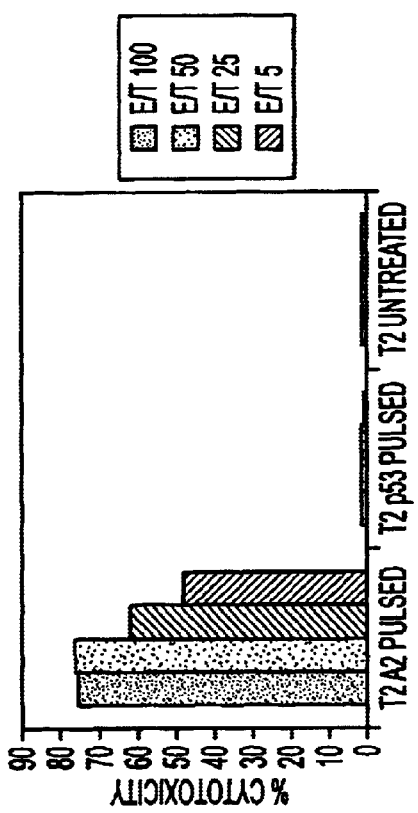
Figure 6D:
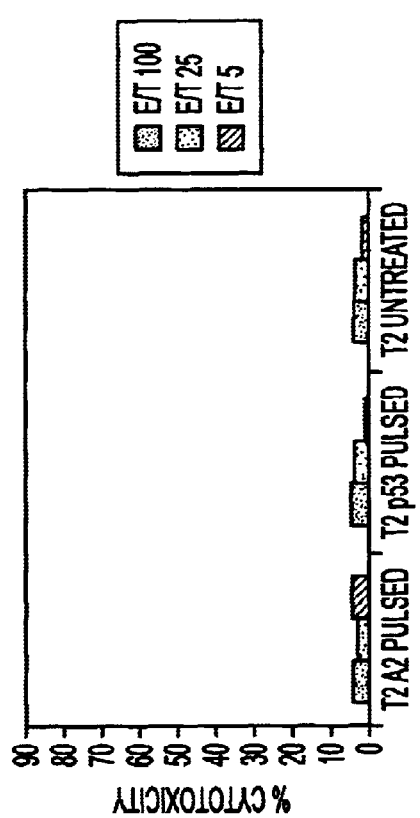

Mice were vaccinated as described in Example 17 with four different formulations of a vaccine containing (Pam)$_2$—KSSAKXVAAWTLKAAANLVPMVATV wherein X signifies cyclohexylalanine (SEQ ID NO:37). Splenocytes were assayed. Effector-to-target ratios in the chromium release assays were as indicated in FIG. 5, where the results are shown. FIG. 5A provides results for mice innoculated with 100 nmoles peptide in a solution containing 99.9% DMSO and 0.1% formic acid. FIG. 5B shows data for mice vaccinated with 100 nmoles peptide suspended in a vehicle containing 50% DMSO, 49.9% PBS and 0.1% formic acid. FIG. 5C refers to mice injected with 83.3 nmoles peptide dissolved in 41.7% DMSO, 57.7% PBS and 0.6% formic acid. FIG. 5D provides results for mice injected with 83.3 nmoles peptide suspended in 66.7% DMSO, 26.7% acetic acid and 6.7% Tween 20. The 99.9% DMSO solution vaccine provided mice splenocytes having the greatest cytotoxicity versus control.

EXAMPLE 19

Vaccination of Transgenic Mice with Monolipidated Vaccine Containing PADRE

Mice were vaccinated and the cells assayed as described above with increasing amounts of (Pam)$_2$—

KSSAKXVAAWTLKAAANLVPMVATV (wherein X signifies cyclohexylalanine (SEQ ID NO:37). The peptide was provided in a solution in 80% DMSO, 20% PBS and 0.08% formic acid in the amounts shown in FIG. 6. Vaccination with 100 or 150 nmoles peptide resulted in potent specific cytotoxicity, with 150 nmoles providing superior results.

EXAMPLE 20

Specificity of Cytotoxicity

Figure 7B:
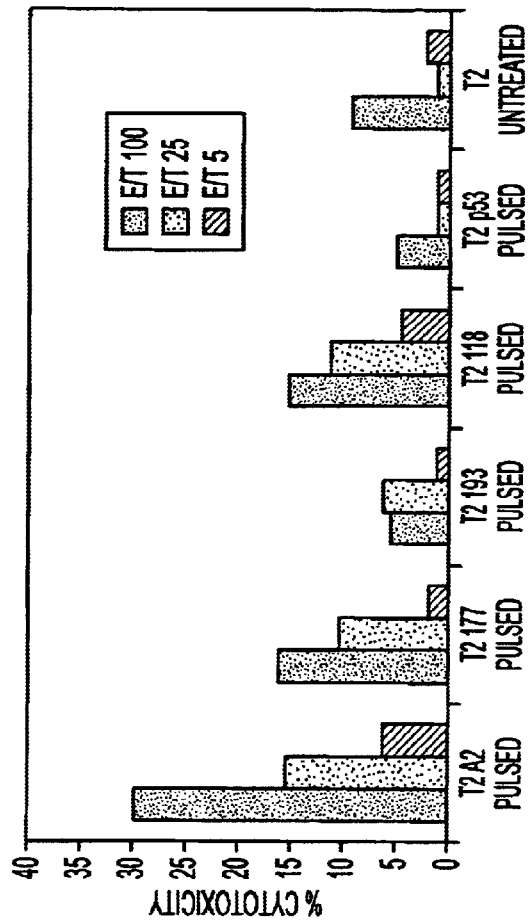
FIG. 7 shows comparative cytotoxicity data for cells from mice immunized with 100 or 25 nmoles SEQ ID NO:37.
Figure 7A:
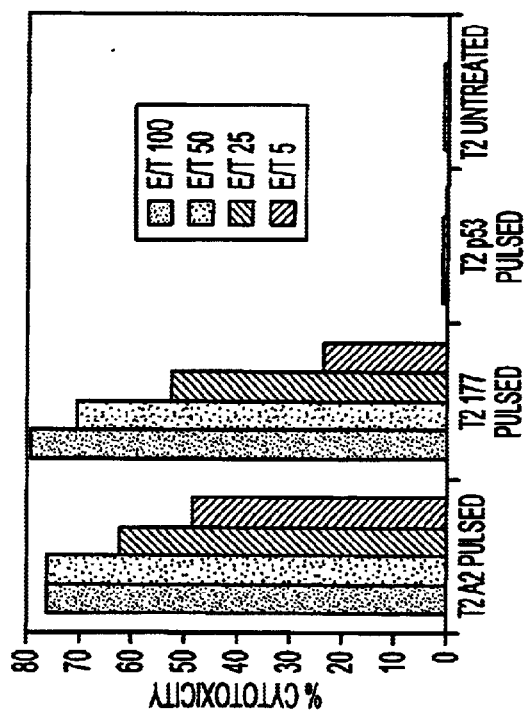

Mice were vaccinated as described above with 150 or 25 nmoles of the peptide of SEQ ID NO:37 formulated as in Example 19. Splenocytes were assayed for cytotoxicity of T2 cells pulsed with and presenting several different peptides. See FIG. 7. "T2 177 pulsed" indicates cells presenting the amidated peptide of SEQ ID NO:39 (NLVPMVATV-NH₂); and "T2 118 pulsed" indicates cells presenting the amidated peptide of SEQ ID NO:40 (YLVPMVASV-NH₂). "T2 193 pulsed" indicates cells presenting the amidated peptide of SEQ ID NO:41 (YLVPMVATV-NH₂). The results showed a high degree of specificity.

EXAMPLE 21

Comparative Data for Monolipidated Vaccine in Different DMSO Formulations

Mice were immunized and their splenocytes assayed as described in Example 17 with 100 or 150 nmoles SEQ ID NO:37 in vehicles containing different DMSO concentrations. See FIG. 8 for the results of chromium release assays. FIG. 8A: 100 nmoles in 80% DMSO, 20% PBS and 0.08% formic acid; FIG. 8B: 100 nmoles in 80% DMSO, 60% PBS and 0.04% formic acid; FIG. 8C: 150 nmoles in 80% DMSO, 20% PBS and 0.08% formic acid; FIG. 8D: 150 nmoles in 40% DMSO, 60% PBS and 0.04% formic acid. Formulations of the monolipidated vaccines were more potent when provided in sufficient DMSO concentration to completely solubilize the vaccine peptide. Without wishing to be bound by theory, it is believed that concentrations of DMSO which result in complete solubility of the lipidated peptide vaccines provide superior results.

EXAMPLE 22

Vaccination Experiments with Differing DMSO Concentrations

Figure 9A:
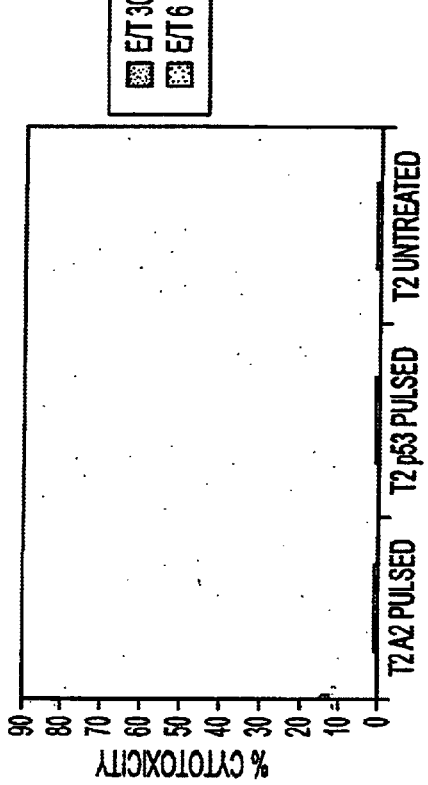
FIG. 9 compares the effectiveness of vaccines containing SEQ ID NO:37 and differing concentrations of DMSO.
Figure 9B:
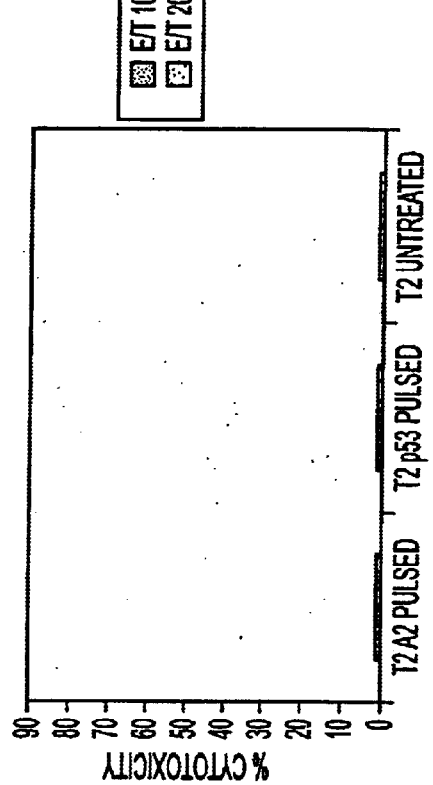
Figure 9C:
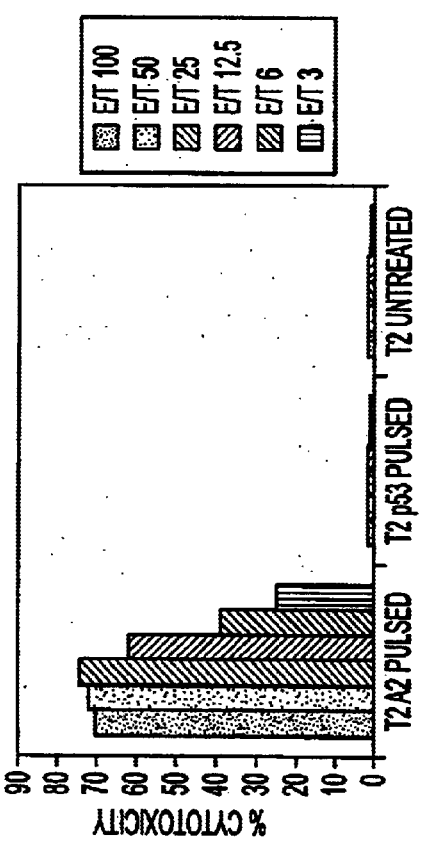
Figure 9D:
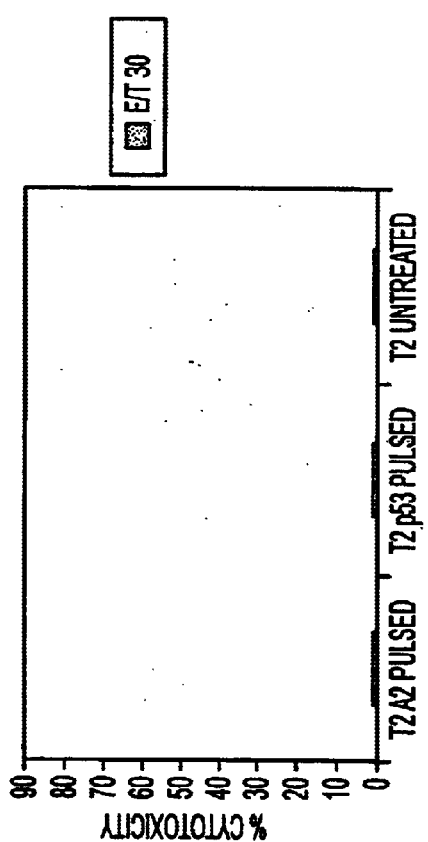

Mice were immunized and their splenocytes assayed as described in Example 17 with 100 nmoles SEQ ID NO:37 in the following vehicles containing decreasing amounts of DMSO. FIG. 9A: 80% DMSO, 20% PBS and 0.02% formic acid; FIG. 9B: 70% DMSO, 30% PBS and 0.07% formic acid; FIG. 9C: 60% DMSO, 40% PBS and 0.06% formic acid; FIG. 9D: 50% DMSO, 50% PBS and 0.02% formic acid. The formulation for FIG. 9A was a solution and the remaining formulations containing less DMSO were suspensions. The results in FIG. 9D reflect mice which received a booster, whereas the remaining panels of FIG. 9 present data from mice receiving one vaccination only. These data confirm the hypothesis that the vaccine should be fully solubilized for best results.

EXAMPLE 23

Vaccination Experiments with Different DMSO Concentrations

Figure 10A:
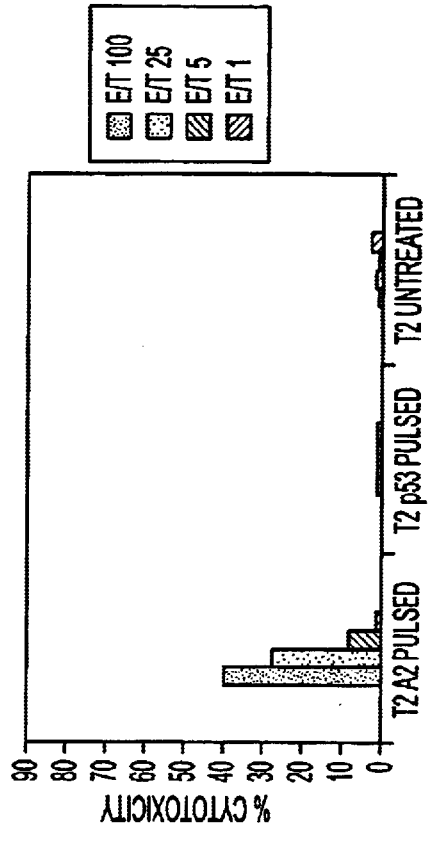
FIG. 10 compares cytotoxicity data from cells immunized with different vaccine formulations of SEQ ID NO:37.
Figure 10B:
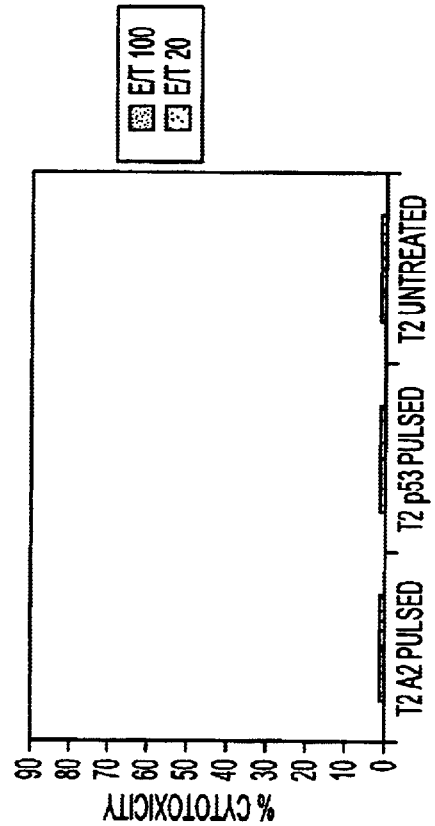
Figure 10C:
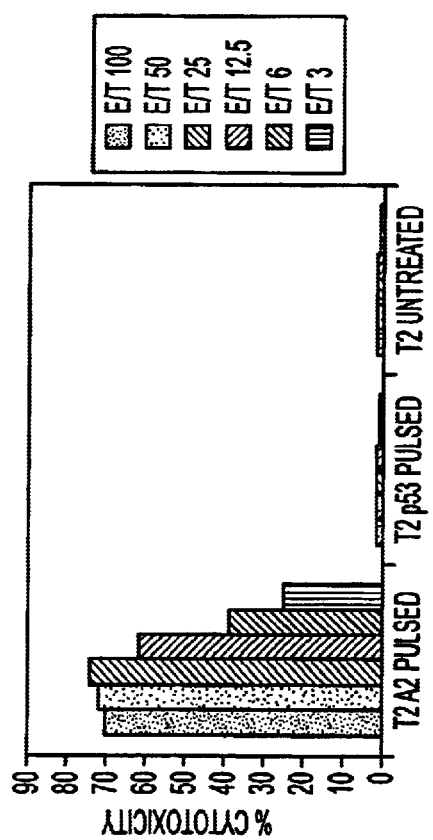
Figure 10D:
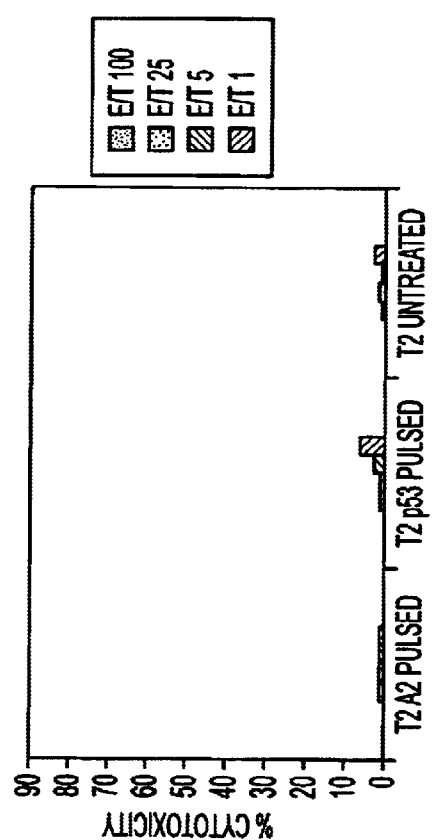

The method of Example 22 was repeated using the following formulations. FIG. 10A: 80% DMSO, 20% PBS and 0.02% formic acid; FIG. 10B: 70% DMSO, 30% PBS and 0.02% formic acid; FIG. 10C: 60% DMSO, 40% PBS and 0.02% formic acid; FIG. 10D: 50% DMSO, 50% PBS and 0.02% formic acid. As before, the vaccine preparation used to produce the data in FIG. 10A was a solution while the remaining formulations were suspensions. The mice providing the splenocytes assayed in FIG. 10D received a booster immunization.

EXAMPLE 24

Effect of Booster Immunizations

Figure 11B:
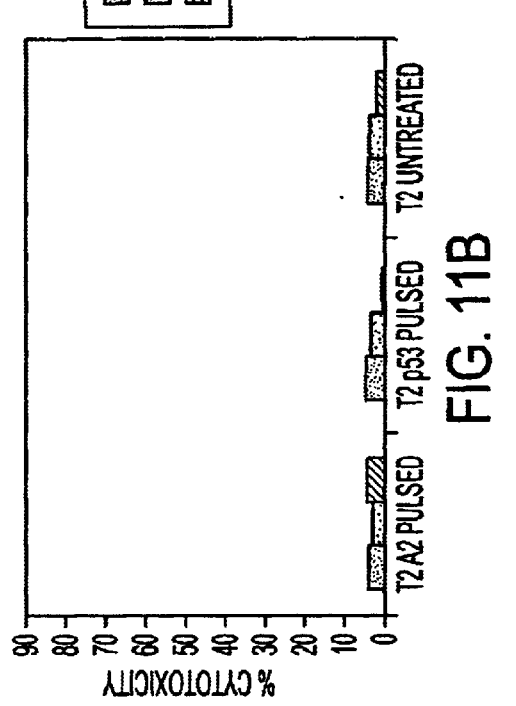
FIG. 11 compares cytotoxicity data from cells immunized with 25 or 50 nmoles SEQ ID NO:37 with or without a booster immunization.
Figure 11D:
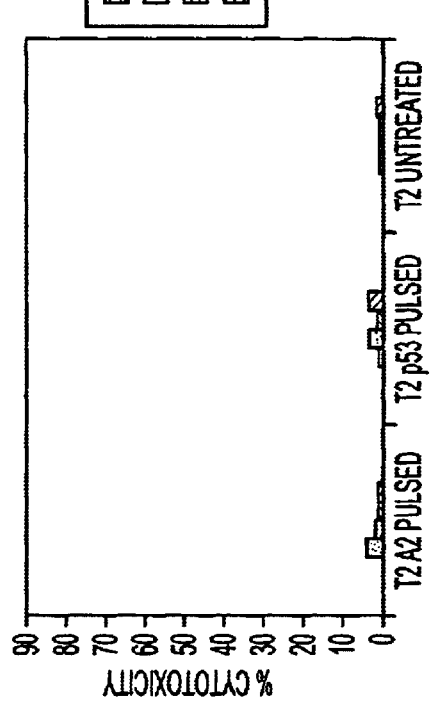
Figure 11A:
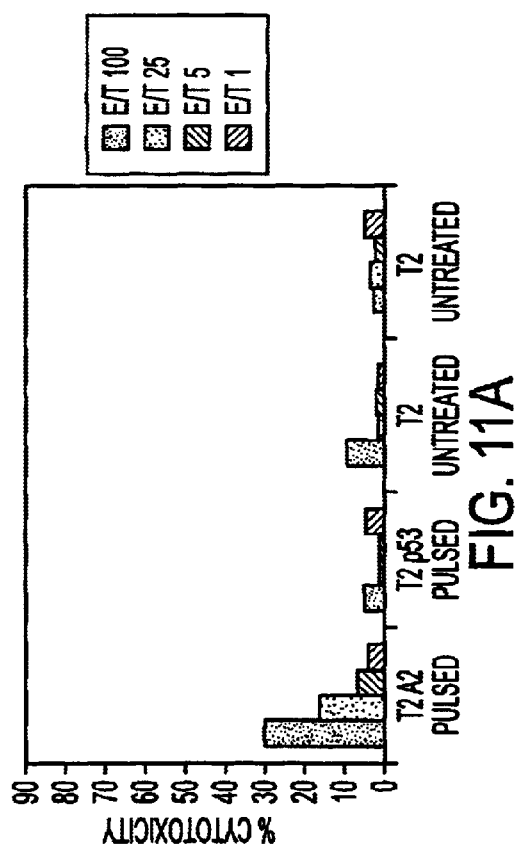
Figure 11C:
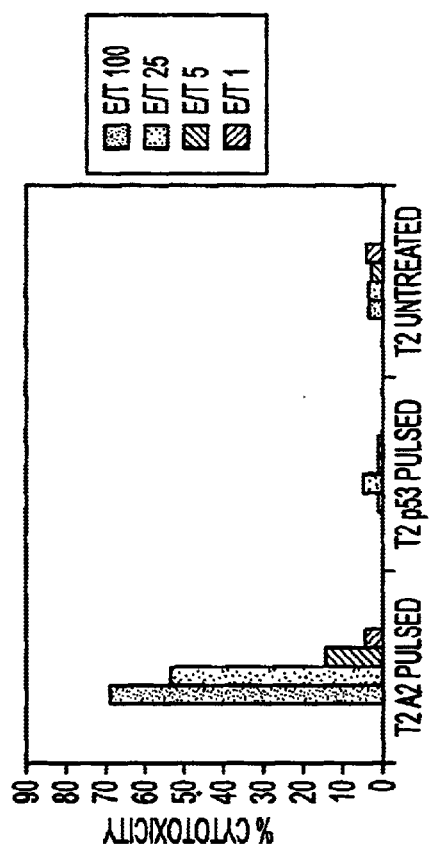

Mice were immunized and their splenocytes assayed as described in Example 17 using one or two immunizations of 25 or 50 nmoles SEQ ID NO:37. See the results in FIG. 11. FIG. 11A: 50 nmoles; FIG. 11B: 25 nmoles; FIG. 11C: 50 nmoles, plus one booster; FIG. 11D: 50 nmoles, plus one booster. A booster injection increased the cytotoxic effects achieved by the immunization for the 50 nmole dose, but apparently provided little or no improvement for the 25 nmole dose.

EXAMPLE 25

Effect of Variable Formic Acid Concentrations

Figure 12A:
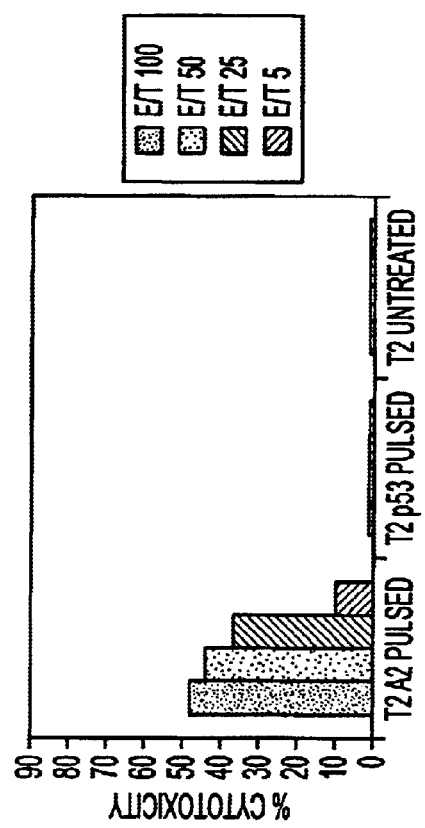
FIG. 12 compares cytotoxicity data from cells immunized with SEQ ID NO:37 in different formulations.
Figure 12B:
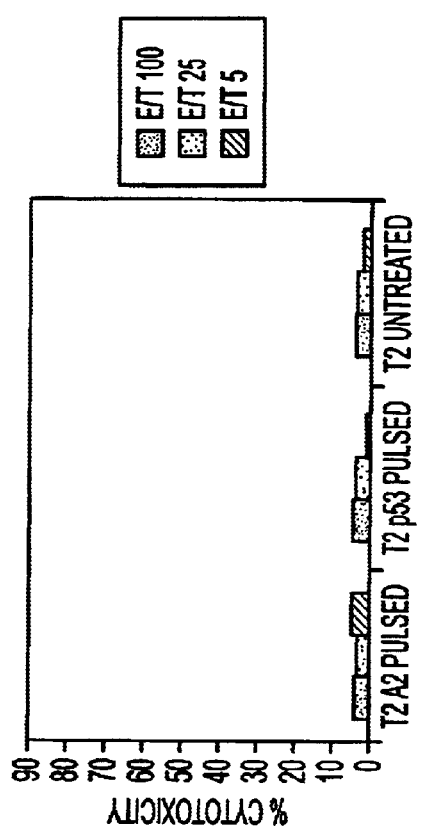
Figure 12C:
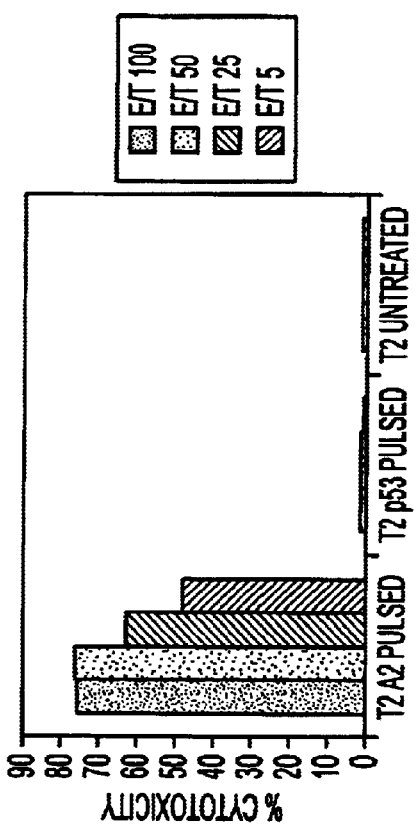
Figure 12D:
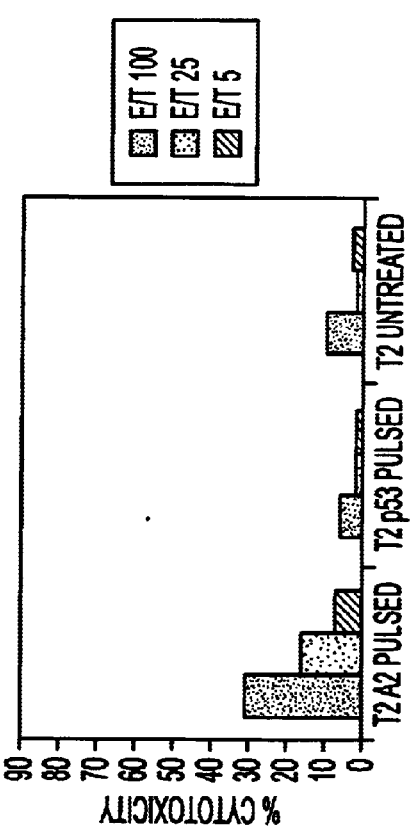

Mice were immunized and their splenocytes were assayed as described in Example 17 using one immunization of SEQ ID NO:37 in 80% DMSO, 20% PBS, containing 0.08% formic acid (FIGS. 12A and 12B) or 0.02% formic acid (FIGS. 12C and 12D). The amount of peptide injected was 150 nmoles (FIG. 12A), 100 nmoles (FIG. 12B), 50 nmoles (FIG. 12C) or 25 nmoles (FIG. 12D). Larger doses clearly resulted in higher specific cytotoxicity after vaccination.

EXAMPLE 26

Vaccination Using Unlipidated Peptide Linked to PADRE

Mice were immunized and their splenocytes assayed as described in Example 17 using one injection of the HCMV peptide of SEQ ID NO: 1, directly linked to PADRE to form one sequence (100 nmol; KSSAKXVAAWTLKAAANLVP-MVATV wherein X is cyclohexylalanine; SEQ ID NO:37) emulsified with incomplete Freund's adjuvant. The vaccine administered was 100 µL of an emulsion containing 5% DMSO, 45% normal saline and 50% incomplete Freund's adjuvant. Tested using T2 cells presenting the peptide of SEQ ID NO:1 stimulated twice in the presence of 10% Rat-Stim, the immunized splenocytes exhibited a specific cytotoxicity of 11.22% at an E/T ratio of 100 and 3.18% at an E/T ratio of 20. The immunized splenocytes exhibited an average % cytotoxicity of −4.44% and −0.10% for T2 cells presenting the control p53 peptide, 3.31% and 3.44% for T2 cells presenting the peptide of SEQ ID NO:39, and −6.39% and −1.81% for untreated T2 cells.

EXAMPLE 27

Vaccination using Unlipidated Linked Peptide in a DNA Adjuvant

Two mice were immunized once with 100 nmoles the peptide of SEQ ID NO:44 with 50 µg DNA adjuvant containing CpG sequences (positive DNA adjuvant). The DNA sequence used was (1826) 5' TCCATGACGTTCCT-GACGTT 3' (SEQ ID NO:42), as described in Z. Moldoveanu, Vaccine 16(11/12):1216–1224 (1998). The chromium release assay data from these immunized splenocytes are provided below in Table 7.

EXAMPLE 28

Vaccination using Unlipidated Linked Peptide in a DNA Adjuvant

Example 27 was repeated using a DNA adjuvant which lacked CpG sequences (negative DNA adjuvant). The DNA sequence used was (1982) 5' TCCAGGACTTCTCTCAG-GTT 3' (SEQ ID NO:43), as described in Z. Moldoveanu, *Vaccine* 16(11/12):1216–1224 (1998). The chromium release assay data are presented below in Table 7.

TABLE 7

Cytotoxicity of Cells Immunized with Unlipidated Linked Peptide Vaccine in DNA Adjuvant

|  | Presented Peptide | % Cytotoxicity E/T = 100 | % Cytotoxicity E/T = 20 |
|---|---|---|---|
| Positive DNA Adjuvant | A2 | 54.72% | 27.79% |
|  | 177 | 13.23% | 3.32% |
|  | p53 | −4.87% | −2.61% |
|  | untreated | −6.24% | 2.77% |

TABLE 7-continued

Cytotoxicity of Cells Immunized with Unlipidated Linked Peptide Vaccine in DNA Adjuvant

|  | Presented Peptide | % Cytotoxicity E/T = 100 | % Cytotoxicity E/T = 20 |
|---|---|---|---|
| Negative DNA Adjuvant | A2 | 45.57% | 18.34% |
|  | 177 | 22.25% | 9.55% |
|  | p53 | −3.46% | −5.82% |
|  | untreated | 1.52% | 2.64% |

Although certain preferred embodiments and examples of the invention have been described, the invention is not so limited. Persons skilled in this field of science will understand that the present invention is capable of wide application in the fields of diagnostics and therapeutics, and that modifications and variations can be made to the invention without departing from its spirit and scope.

I claim:

1. Enriched activated HCMV-reactive T cells that recognize a peptide of SEQ ID NO:1.

2. A method of preparing activated HCMV-reactive T cells according to claim 1 which comprises incubating T cells with antigen presenting cells that present a peptide of SEQ ID NO:1.

3. Activated HCMV-reactive T cells prepared according to the method of claim 2.

4. A method of augmenting HCMV immunity in a mammal in need thereof which comprises administering to said mammal activated HCMV-reactive T cells prepared according to the method of claim 2.

5. A method according to claim 4, wherein said activated HCMV-reactive T cells are autologous to said mammal.

6. A method according to claim 4, wherein said activated HCMV-reactive T cells are autologous to said mammal.

* * * * *

UNITED STATES PATENT AND TRADEMARK OFFICE
CERTIFICATE OF CORRECTION

PATENT NO. : 6,727,093 B2
APPLICATION NO. : 10/238607
DATED : April 27, 2004
INVENTOR(S) : Diamond It is certified that error appears in the above-identified patent and that said Letters Patent is hereby corrected as shown below:

Column 1, line 4, after "prior" insert --co-pending--;
Column 1, line 6, after "prior" insert --co-pending--;
Column 48, line 15, claim 5, replace "autologous" with --allogeneic--.

Signed and Sealed this

Eighth Day of August, 2006

JON W. DUDAS
*Director of the United States Patent and Trademark Office*